(12) United States Patent
Shaver et al.

(10) Patent No.: US 11,948,664 B2
(45) Date of Patent: Apr. 2, 2024

(54) AUTOENCODER WITH GENERATIVE ADVERSARIAL NETWORK TO GENERATE PROTEIN SEQUENCES

(71) Applicant: Just-Evotec Biologics, Inc., Seattle, WA (US)

(72) Inventors: Jeremy Martin Shaver, Lake Forest Park, WA (US); Tileli Amimeur, Seattle, WA (US); Randal Robert Ketchem, Snohomish, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 0 days.

(21) Appl. No.: 18/027,577

(22) PCT Filed: Sep. 21, 2021

(86) PCT No.: PCT/US2021/051325
§ 371 (c)(1),
(2) Date: Mar. 21, 2023

(87) PCT Pub. No.: WO2022/061294
PCT Pub. Date: Mar. 24, 2022

(65) Prior Publication Data
US 2023/0335222 A1    Oct. 19, 2023

Related U.S. Application Data

(60) Provisional application No. 63/081,050, filed on Sep. 21, 2020.

(51) Int. Cl.
*G16B 40/20* (2019.01)
*G06N 3/0455* (2023.01)
(Continued)

(52) U.S. Cl.
CPC ........... *G16B 40/20* (2019.02); *G06N 3/0455* (2023.01); *G06N 3/0475* (2023.01); *G16B 40/30* (2019.02)

(58) Field of Classification Search
None
See application file for complete search history.

(56) References Cited

U.S. PATENT DOCUMENTS

| 2013/0324477 A1 | 12/2013 | Bernard et al. |
| 2015/0213193 A1 | 7/2015 | Apte et al. |

(Continued)

FOREIGN PATENT DOCUMENTS

| EP | 3051450 A1 | 8/2016 |
| WO | WO-2022061294 A1 | 3/2022 |

OTHER PUBLICATIONS

"International Application Serial No. PCT/US2021/051325, International Search Report dated Dec. 16, 2021", 2 pgs.

(Continued)

*Primary Examiner* — Leon Viet Q Nguyen
(74) *Attorney, Agent, or Firm* — Schwesman Lundberg & Woessner, P.A.

(57) ABSTRACT

Amino acid sequences of proteins can be produced using an autoencoder. For example, amino acid sequences of variant proteins can be produced by an autoencoder that is fed an amino acid sequence of a base protein as input. A decoding component of the autoencoder can include at least one or more components of a generative adversarial network.

15 Claims, 7 Drawing Sheets

(51) Int. Cl.
G06N 3/0475 (2023.01)
G16B 40/30 (2019.01)

(56) References Cited

U.S. PATENT DOCUMENTS

| 2017/0328194 | A1 | 11/2017 | Liu et al. | |
|---|---|---|---|---|
| 2019/0197358 | A1 | 6/2019 | Madani et al. | |
| 2020/0273541 | A1* | 8/2020 | Costello | G16B 40/20 |
| 2022/0122692 | A1* | 4/2022 | Feala | G16B 40/20 |

OTHER PUBLICATIONS

"International Application Serial No. PCT/US2021/051325, Written Opinion dated Dec. 16, 2021", 5 pgs.

Li, et al., "Grass: Generative recursive autoencoders for shape structures", ACM Transactions on Graphics (TOG) 36.4 (2017), Retrieved on Nov. 12, 2021 from: <https://dl.acm.org/doi/abs/10.1145/3072959.3073637>, (Jul. 20, 2017), 1-14.

"International Application Serial No. PCT US2021 051325, International Preliminary Report on Patentability dated Mar. 30, 2023", 7 pgs.

"European Application Serial No. 21870417.9, Extended European Search Report dated Jan. 31, 2024", 4 pgs.

Anand, Namrata, et al., "Generative Modeling for Protein Structures", [Online] Retrieved from the internet: <https//proceedings.neurips.cc/paper_files/paper/2018/file/afa299a4dld8c52e75dd8a24c3ce 534f-Paper.pdf>, (Jan. 1, 2018), 12 pgs.

Yuyang, Wang, et al., "Bio-informed Protein Sequence Generation for Multi-class Virus Mutation Prediction", [Online] Retrieved from the internet: <https://www.biorxiv.org/content/10.1101/2020.06.11.146167v1.full.pdf>, (Jun. 12, 2020), 15 pgs.

* cited by examiner

AUTOENCODER WITH GENERATIVE ADVERSARIAL NETWORK TO GENERATE PROTEIN SEQUENCES

CROSS-REFERENCE TO RELATED APPLICATION(S) AND PRIORITY CLAIM

This application is a U.S. national stage filing under 35 U.S.C. 371 from International Application No. PCT/US2021/051325, filed on 21 Sep. 2021, and published as WO 2022/061294 A1 on 24 Mar. 2022, which claims priority to U.S. Provisional Application No. 63/081,050 filed on 21 Sep. 2020 and entitled "Autoencoder with Generative Adversarial Network to Generate Protein Sequences," the entirety of which are incorporated herein by reference.

BACKGROUND

Proteins are biological molecules that are comprised of one or more chains of amino acids. Proteins can have various functions within an organism. For example, some proteins can be involved in causing a reaction to take place within an organism. In other examples, proteins can transport molecules throughout the organism. In still other examples, proteins can be involved in the replication of genes. Additionally, some proteins can have therapeutic properties and be used to treat various biological conditions. The structure and function of proteins are based on the arrangement of amino acids that comprise the proteins. The arrangement of amino acids for proteins can be represented by a sequence of letters with each letter corresponding to an amino acid at a respective position. The arrangement of amino acids for proteins can also be represented by three dimensional structures that not only indicate the amino acids at various locations of the protein, but also indicate three dimensional features of the proteins, such as an α-helix or a β-sheet.

BRIEF DESCRIPTION OF THE DRAWINGS

The present disclosure is illustrated by way of example and not limitation in the figures of the accompanying drawings, in which like references indicate similar elements.

DETAILED DESCRIPTION

Figure 1:
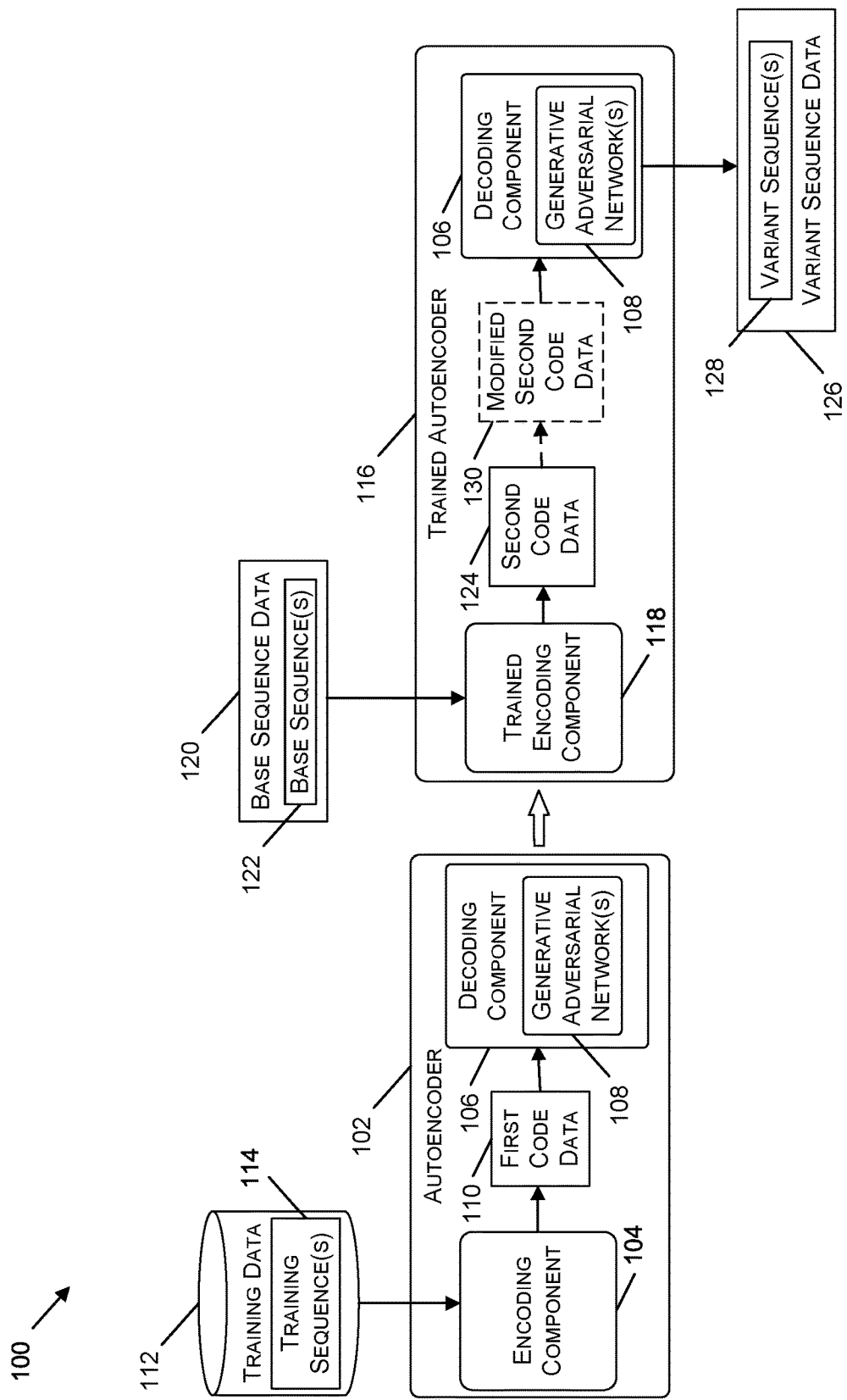
FIG. 1 is a diagram illustrating an example framework to generate an autoencoder that includes a decoding component that implements one or more components of a generative adversarial network, in accordance with some implementations.

Proteins can have many beneficial uses within organisms. In particular situations, proteins can be used to treat diseases and other biological conditions that can detrimentally impact the health of humans and other mammals. In various scenarios, proteins can participate in reactions that are beneficial to subjects and that can counteract one or more biological conditions being experienced by the subjects. In some examples, proteins can also bind to target molecules within an organism that may be detrimental to the health of a subject. For these reasons, many individuals and organizations have sought to develop proteins that may have therapeutic benefits.

The development of proteins can be a time consuming and resource intensive process. Often, candidate proteins for development can be identified as potentially having various biophysical properties, structural features (e.g., negatively charged patches, hydrophobic patches), three-dimensional (3D) structures, and/or behavior within an organism. In order to determine whether the candidate proteins actually have the characteristics of interest, the proteins can be synthesized and then tested to determine whether the actual characteristics of the synthesized proteins correspond to the desired characteristics. Due to the amount of resources needed to synthesize and test proteins for specified biophysical properties, structural features, 3D structures, and/or behaviors, the number of candidate proteins synthesized for therapeutic purposes is limited. In some situations, the number of proteins synthesized for therapeutic purposes can be limited by the loss of resources that takes place when candidate proteins are synthesized and do not have the desired characteristics.

The techniques, methods, and systems described herein can include using an autoencoder to produce amino acid sequences of variants of a base protein. The autoencoder can include an encoding component and a decoding component. The encoding component can include a first number of computational layers, such as a first number of convolutional layers, and the decoding component can include a second number of computational layers, such as a second number of convolutional layers. The encoding component can produce code data that is a representation of input data provided to the encoding component. The code data can be provided to the decoding component and the decoding component can produce output that corresponds to the code data.

The decoding component can include one or more components of a generative adversarial network. For example, the decoding component can include at least a generating component of a generative adversarial network. In various implementations, the generative adversarial network can be trained prior to the training of the autoencoder. The generative adversarial network can be trained using a set of training data that corresponds to amino acid sequences of proteins.

At least a trained generating component of the generative adversarial network can be implemented as a decoding component for the autoencoder. Additionally, the trained generating component of the generative adversarial network can produce a training dataset that can be used to train the autoencoder.

During the training of the autoencoder, the computational layers of the encoding component can be modified while the computational layers of the decoding component are not modified. The training of the autoencoder can include comparing output data produced by the decoding component with input data provided to the encoding component. In one or more illustrative examples, output data corresponding to amino acid sequences produced by the decoding component can be analyzed with respect to input data corresponding to amino acid sequences included in the training dataset. Based on differences between the output of the decoding component and the input provided to the encoding component, modifications can be made to the encoding component. For example, at least one of weights, functions, or parameters of the computational layers of the encoding component can be modified based on the differences between the output data produced by the decoding component and the input data provided to the encoding component until the differences are minimized. In various examples, the weights, functions, and/or parameters of the computational layers of the decoding component can remain fixed during the training of the autoencoder. In this way, the training of the autoencoder according to implementations described herein can utilize fewer computational resources than existing techniques for the training of autoencoders that modify features of the computational layers of both the encoding component and the decoding component.

After training, the autoencoder, base sequence data can be provided to the encoding component. The base sequence data can correspond to an amino acid sequence of a base protein. The encoder can produce code data that is a representation of the base sequence data. The decoding component can generate variant protein sequences based on the code data. In one or more examples, the code data can be modified, and the modified code data can be provided to the decoding component. The decoding component can then use the modified code data to generate variant sequence data that corresponds to amino acid sequences of variants of the base protein. In one or more additional examples, the decoding component can generate variant sequence data based on the code data without modification of the code data. To illustrate, the code data can be processed multiple times by the decoding component and the decoding component can generate data corresponding to different amino acid sequences of variants of the base protein for individual passes of the code data through the decoding component. As used herein, variant, variant protein, and similar terms can refer to a protein that differs from a base protein at one or more positions. For example, an amino acid sequence of a base protein can indicate amino acids located at a number of positions of the base protein and a variant of the base protein can include at least one position having an amino acid that is different from the base protein at the same, corresponding position. The variants of the base protein can have at least a threshold amount of identity with the base protein.

In one or more examples, transfer learning techniques can be implemented such that an autoencoder can produce variants of a base protein that have one or more characteristics of interest. The transfer learning can be implemented with respect to a generative adversarial network that includes a generating component that comprises the decoding component of the autoencoder. In these scenarios, the training data used in the transfer learning process for the generative adversarial network can include a number of amino acid sequences of proteins having the one or more characteristics of interest. In various examples, transfer learning can be implemented to cause the autoencoder to produce variants of a base protein that have one or more structural features of interest. In one or more illustrative examples, transfer learning can be implemented such that the autoencoder can generate amino acid sequences of proteins having one or more polar regions having a specified range of amino acids included in each polar region. Additionally, transfer learning can be implemented to cause the autoencoder to produce variants of the base protein that have one or more biophysical properties of interest. To illustrate, transfer learning can be used to produce an autoencoder that generates amino acid sequences of proteins that have at least a threshold melting temperature.

The implementations described herein that include training a generative adversarial network and then training an autoencoder that includes the generating component of the generative adversarial network as a decoding component can result in increased efficiency with respect to training the autoencoder. For example, since the decoding component has already been trained to generate amino acid sequences having a set of characteristics, a reduction in the adjustments to the encoding component during training is realized in relation to a situation where the encoding component and the decoding component are being trained concurrently. To illustrate, a generative adversarial network can be trained to generate amino acid sequences that have characteristics of antibodies. In these situations, since the decoding component is already trained to produce amino acid sequences of antibodies, the encoding component is able to be trained more quickly and efficiently to produce amino acid sequences that include characteristics of antibodies based on the feedback obtained from the decoding component. Further, training a generating component of a generative adversarial network as a decoding component of an autoencoder to produce amino acid sequences of antibodies can cause higher order interactions of the antibodies to be embedded in the weights of the generating component and, in this way, modifications to the code data can produce variant amino acid sequences that have chemically relevant changes that may be difficult to predict from first order principles.

In addition, the systems, techniques, architectures, and processes described herein can be implemented such that changes to the code data can result in linear or generally linear changes of one or more variant amino acid sequences produced with respect to one or more base sequences. For example, relatively small changes to the code data can result in relatively small changes to the variant amino acid sequences in relation to base amino acid sequences while relatively large changes to the code data can result in relatively large changes to the variant amino acid sequences in relation to the base amino acid sequences. In this way, the amount of variation produced in the variant sequences can be controlled to a greater degree than existing systems and processes. Also, manual modifications made to an input amino acid sequence can be realized in the code data in such a way that changes to amino acids at other positions of the input sequence that may be necessitated by the initial, manual change(s) are produced in the variant amino acid sequences. To illustrate, to preserve one or more characteristics of amino acid sequences produced by the decoding component, the encoding component can modify the code data such that variant amino acid sequences of a parent amino acid sequence that has been manually modified in at least one position also have the one or more characteristics.

As used herein, structural features of proteins can refer to features of one or more amino acids or features of one or more groups of amino acids included in a protein molecule. Examples of structural features can include at least one of hydrophobic regions that include one or more amino acids, negatively charged regions that include one or more amino acids, positively charged regions that include one or more amino acids, basic regions that include one or more amino acids, acidic regions that include one or more amino acids, regions that include one or more aromatic amino acids, neutral regions that include one or more amino acids, a measure of diversity of neighboring residues, a measure of residues interacting in ionic bonds, or regions of amino acids participating in at least one of an α-helix, a β-turn, a β-sheet, or an Ω-loop. In addition, as used herein biophysical properties of proteins can refer to characteristics that can be measured with respect to a protein molecule. Examples of biophysical properties of proteins can include at least one of melting temperature, unfolding temperature, measures of aggregation, measures of stability, measures of molecular weight, measures of interactions between regions as determine by self-interaction nanoparticle spectroscopy (SINS), measures of viscosity, or measures of solubility.

FIG. 1 is a diagram illustrating an example framework 100 to generate an autoencoder that includes a decoding component that implements one or more components of a generative adversarial network, in accordance with some implementations. The framework 100 can include an autoencoder 102 that comprises an encoding component 104 and a decoding component 106. The autoencoder 102 can comprise at least one of autoencoder computer-readable instructions, autoencoder logic, or autoencoder circuitry. In addition, the encoding component 104 can include at least one of encoding computer-readable instructions, encoding logic, or encoding circuitry. Further, the decoding component 106 can include at least one of decoding computer-readable instructions, decoding logic, or decoding circuitry.

The encoding component 104 can include first computational layers with each first computational layer comprising a number of nodes that each have at least one function and one or more weights. The decoding component 106 can include second computational layers with each second computational layer comprising a number of nodes that each have at least function and one or more weights. In various examples, a portion of the first computational layers and a portion of the second computational layers can include fully connected layers. In one or more examples, at least a portion of the functions and/or weights of the first computational layers can be different with respect to the functions and/or weights of the second computational layers. The decoding component 106 can include at least a portion of one or more generative adversarial networks 108. For example, the decoding component 106 can include a generating component of the one or more generative adversarial networks 108. The encoding component 104 and/or the decoding component The one or more generative adversarial networks 108 can include at least one of generative adversarial network computer-readable instructions, generative adversarial network logic, or generative adversarial network circuitry.

The encoding component 104 can generate first code data 110 that is a representation of input provided to the encoding component 104. The first code data 110 can correspond to a compressed version of input data provided to the encoding component 104. The first code data 110 is provided to the decoding component 106. The decoding component 106 can generate output of the autoencoder 102 based on the first code data 110. In various examples, the decoding component 106 can generate output data that corresponds to the input data provided to the encoding component 104.

The autoencoder 102 can undergo a training process using training data 112. The training of the autoencoder 102 can include training of the encoding component 104. In one or more examples, the decoding component 106 can be trained before the training of the encoding component 104 using the training data 112 takes place. That is, the one or more generative adversarial networks 108 can be trained outside of a training process for the autoencoder 102. In various examples, the one or more generative adversarial networks 108 can be trained to generate sequence data that corresponds to amino acid sequences of proteins. In these scenarios, the encoding component 104 can be trained to produce the first code data 110 that can be provided to the decoding component 106 to generate the sequence data. In one or more illustrative examples, the training data 112 can include training sequences 114 that correspond to a number of amino acid sequences of proteins. In one or more additional implementations, at least a portion of the training data 112 can be produced by the one or more generative adversarial networks 108. The training data 112 can be stored by one or more data stores that are accessible to the autoencoder 102.

During the training of the encoding component 104, a training sequence 114 can be provided to the encoding component 104 and the encoding component 104 can generate the first code data 110 that is a representation of the training sequence 114. In one or more illustrative examples, the first code data 110 can include a compressed version of the training sequence 114 that utilizes less data to represent the training sequence 114 than the initial data included in the training data 112 that was used to represent the training sequence 114. The first code data 110 can then be provided to the decoding component 106 and the decoding component 106 can generate output based on the first code data 110. The output generated by the decoding component 106 can include an output sequence that can be analyzed with respect to the training sequence 114 that the encoding component 104 used to generate the first code data 110. Differences between the output sequence and the training sequence 114 can be used to modify at least one loss function of the autoencoder 102. The training process for the autoencoder 102 can minimize the loss function of the autoencoder 102. In one or more examples, minimizing the loss function of the autoencoder 102 can include minimizing differences between the output sequences generated by the decoding component 106 and the training sequences 114 obtained by the encoding component 104. In at least some implementations, the training of the autoencoder 102 can be complete when at least a threshold percentage of output sequences produced by the decoding component 106 have less than a threshold number of differences with respect to corresponding training sequences 114 used by the encoding component 104 to produce the first code data 110. In one or more additional examples, the encoding component 104 can be trained using training sequences 114 that the decoding component 106 is unable to reproduce. In these instances, the training of the encoding component 104 can be complete in response to determining that the loss function of the autoencoder 102 has been minimized.

After training of the autoencoder 102 is complete, a trained autoencoder 116 can be produced. The trained autoencoder 116 can include a trained encoding component 118 and the decoding component 106. In these implementations, the computational layers of the decoding component 106 have not been modified or have been modified to a relatively minor degree during the training of the autoencoder 102. The trained autoencoder 116 can produce amino acid sequences of variants of base proteins. In one or more illustrative examples, the proteins can include amino acid sequences of fibronectin type III (FNIII) proteins, avimers, antibodies, VHH domains, kinases, zinc fingers, T-cell receptors, combinations thereof, and the like. In various examples, the amino acid sequences produced by the trained autoencoder 116 can include portions of proteins. In one or more implementations, the trained autoencoder 116 can produce amino acid sequences of portions of antibodies, such as at least a portion of one or more complementarity determining regions (CDRs) of antibodies, at least a portion of one or more light chains of antibodies, at least a portion of one or more heavy chains of antibodies, at least a portion of one or more variable regions of antibodies, at least a portion of one or more constant regions of antibodies, at least a portion of one or more hinge regions of antibodies, at least a portion of one or more antigen binding regions of antibodies, one or more combinations thereof, and so forth.

In one or more examples, base sequence data 120 can be obtained by the trained encoding component 118. The base sequence data 120 can include one or more base sequences 122 that correspond to one or more amino acid sequences of one or more base proteins. The trained encoding component 118 can generate second code data 124 based on the base sequence data 120. The second code data 124 can correspond to a representation of the base sequence data 120. In various examples, the second code data 124 can correspond to a compressed version of the base sequence data 120. The decoding component 106 can generate variant sequence data 126 based on the second code data 124. The variant sequence data 126 can include one or more variant sequences 128 that correspond to one or more amino acid sequences of proteins that are variants of the base proteins associated with the base sequences 122. For example, a variant sequence 128 can include at least one amino acid that is different from the amino acid located at the same position in a corresponding base sequence 122.

In situations where the encoding component 104 is trained to produce the first code data 110 such that the decoding component 106 is unable to reproduce the training sequences 114, the second code data 124 may not be modified when provided to the decoding component 106. Thus, the second code data 124 generated by the trained encoding component 118 can be used directly by the decoding component 106 to produce one or more variant sequences 128 that correspond to one or more base sequences 122. In additional scenarios, the second code data 124 can be modified to produce modified second code data 130 that is used by the decoding component 106 to generate one or more variant sequences 128 that correspond to one or more base sequences 122. In one or more illustrative examples, the second code data 124 can include a matrix having a plurality of numerical values. In these instances, the modified second code data 130 can include modifications to one or more of the numerical values included in the matrix. The number of numerical values in the matrix that are modified can correspond to a number of changes in the base sequence 122 that are included in the one or more variant sequences 128. To illustrate, as the number of numerical values modified in the matrix from the second code data 124 to the modified second code data 130 increases, the number of positions of the one or more variant sequences 128 that are different from the corresponding positions in the base sequence 122 can also increase. Additionally, the magnitude of changes to the individual numerical values included in the matrix corresponding to the second code data 124 used to produce the modified second code data 130 can impact the number of positions of the base sequence 122 that are modified in the one or more variant sequences 128 produced based on the modified second code data 130. For example, as the magnitude of changes to individual numerical values of the matrix included in the second code data 124 increases, the number of positions of the base sequence 122 that have amino acids that are modified in relation to the one or more variant sequences 128 can also increase. That is, as at least one of the number of numerical values of the matrix increases or the magnitude of change of individual numerical values of the matrix increases to produce the modified second code data 130, the amount of identity between the one or more base sequences 122 and the one or more variant sequences 128 decreases.

In one or more additional illustrative examples, the individual numerical values included in the matrix can range from −1 to +1. In these scenarios, a number of changes to one or more variant sequences 128 with respect to the one or more base sequences 122 and an amount of change in the individual values of the matrix from the second code data 124 to the modified second code data 130 can indicate a number of differences between the one or more base sequences 122 and the one or more variant sequences 128. For example, an adjustment in one to three numerical values of the second code data 124 by from about 2% to about 5% to produce the modified second code data 130 can produce one or more variant sequences 128 having from about one residue to about ten residues that are different from the one or more base sequences 122. The adjustments to the individual numerical values of the second code data 124 can be produced according to a random or pseudo-random number generating algorithm.

In one or more implementations, after the trained autoencoder 116 is produced, at least one transfer learning process can be performed that can modify the amino acid sequences produced by the one or more generative adversarial networks 108 included in the decoding component 106. For example, the one or more generative adversarial networks 108 can be initially trained to produce amino acid sequences of proteins and, after one or more transfer learning processes are performed, the one or more generative adversarial networks 108 can be trained to produce amino acid sequences having one or more structural features of interest and/or one or more specified biophysical properties of interest. In one or more illustrative examples, after one or more transfer learning processes, the one or more generative adversarial networks 108 can produce amino acid sequences of antibodies that have at least a threshold unfolding temperature. In one or more additional illustrative examples, after one or more transfer learning processes, the one or more generative adversarial networks 108 can produce amino acid sequences of antibodies that have one or more negatively charged patches that include a specified range of numbers of amino acids.

The trained autoencoder 116 can be further trained in response to the one or more generative adversarial networks 108 undergoing one or more transfer learning processes. The further training of the trained autoencoder 116 can produce an additional trained autoencoder that generates amino acid sequences of proteins having the one or more characteristics that were the subject of the one or more transfer learning processes. To illustrate, in scenarios where the one or more generative adversarial networks 108 have been subjected to one or more transfer learning processes to train the one or more generative adversarial networks 108 to generate amino acid sequences of proteins having no greater than a threshold viscosity in water, the trained autoencoder 116 can be further trained to produce variant sequences 128 of proteins that have at least a threshold probability of having no greater than the threshold viscosity in water.

Figure 2:
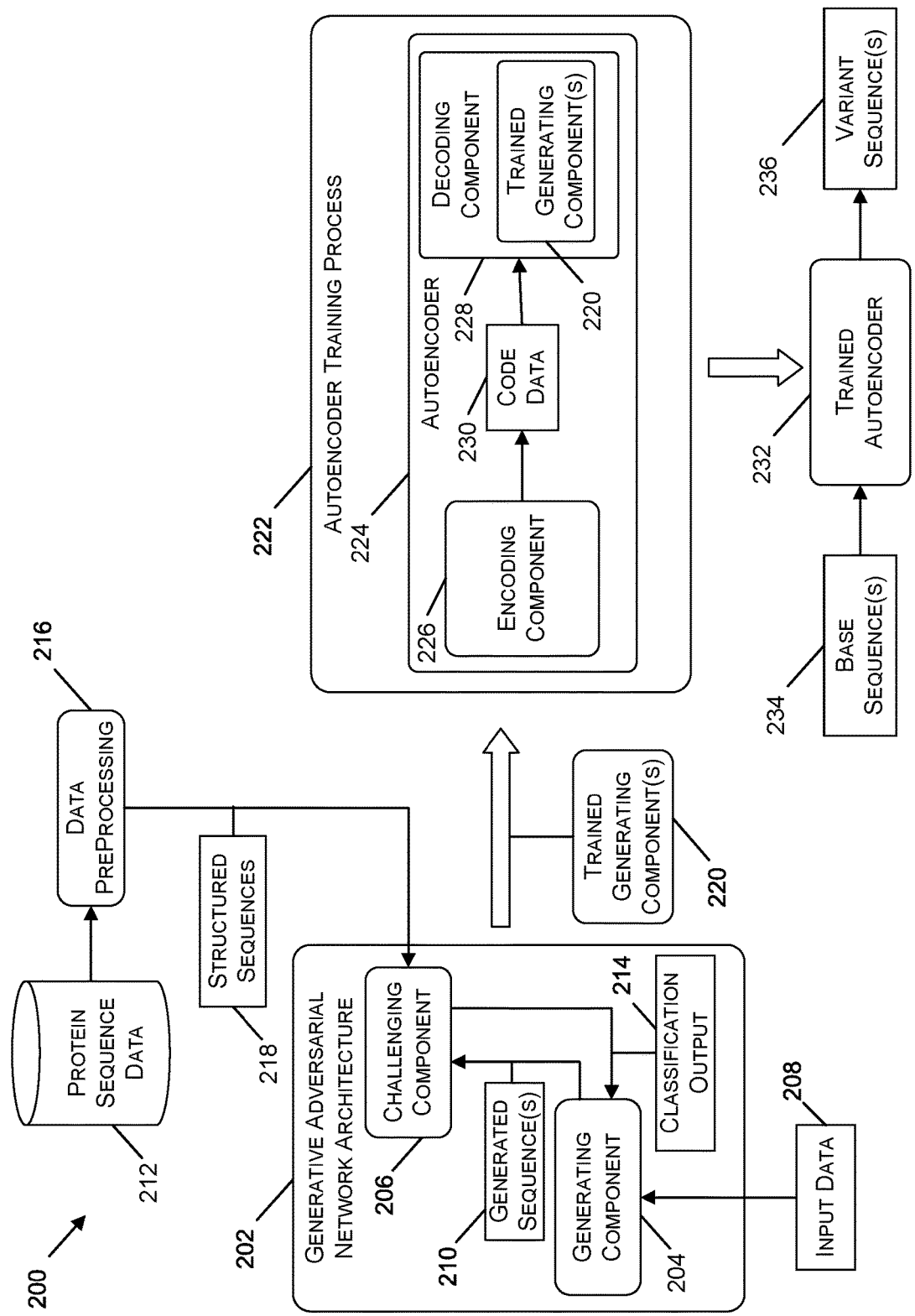
FIG. 2 is a diagram illustrating an example framework to train a generative adversarial network for use as a decoding component of an autoencoder, in accordance with some implementations.

FIG. 2 is a diagram illustrating an example framework 200 to train a generative adversarial network for use as a decoding component of an autoencoder, in accordance with some implementations. The framework 200 can include a generative adversarial network architecture 202. The generative adversarial network architecture 202 can include a generating component 204 and a challenging component 206. The generative adversarial network architecture 202 can include at least one of generative adversarial network computer-readable instructions, generative adversarial network logic, or generative adversarial network circuitry. In addition, the generating component 204 can be implemented using at least one of computer-readable instructions, logic, or circuitry. Further, the challenging component 206 can be implemented using at least one of computer-readable instructions, logic, or circuitry.

The generating component 204 can implement one or more models to generate amino acid sequences based on input provided to the generating component 204. In various implementations, the one or more models implemented by the generating component 204 can include one or more functions and one or more weights. The challenging component 206 can generate output indicating whether the amino acid sequences produced by the generating component 204 correspond to various characteristics. The output produced by the challenging component 206 can be provided to the generating component 204 and the one or more models implemented by the generating component 204 can be modified based on the feedback provided by the challenging component 206. In various implementations, the challenging component 206 can analyze the amino acid sequences generated by the generating component 204 with amino acid sequences of proteins included in training data and generate an output indicating an amount of correspondence between the amino acid sequences produced by the generating component 204 and the amino acid sequences of proteins provided to the challenging component 206 as training data. In one or more illustrative examples, the analysis performed by the challenging component 206 with respect to the amino acid sequences produced by the generating component 204 can include a comparison between the amino acid sequences included in the training data and the amino acid sequences produced by the generating component 204.

In various implementations, the generative adversarial network architecture 202 can implement one or more neural network technologies. For example, the generative adversarial network architecture 202 can implement one or more recurrent neural networks. Additionally, the generative adversarial network architecture 202 can implement one or more convolutional neural networks. In one or more implementations, the generative adversarial network architecture 202 can implement a combination of recurrent neural networks and convolutional neural networks. In one or more additional examples, the generating component 204 can include a generator and the challenging component 206 can include a discriminator. In one or more further implementations, the generative adversarial network architecture 202 can include a Wasserstein generative adversarial network (wGAN). In these scenarios, the generating component 204 can include a generator and the challenging component 206 can include a critic.

In the illustrative example of FIG. 2, an input vector 208 can be provided to the generating component 204 and the generating component 204 can produce one or more generated sequences 210 from the input vector 208 using one or more models. In one or more implementations, the input vector 208 can include noise data that is generated by a random number generator or a pseudo-random number generator. The generated sequence(s) 210 can be compared by the challenging component 206 against sequences of proteins included in protein sequence data 212 that have been structured according to one or more schemas. The protein sequence data 212 can include sequences of proteins obtained from one or more data sources that store amino acid sequences of proteins. The protein sequence data 212 can be training data for the generative adversarial network architecture 202.

Based on similarities and/or differences between the generated sequence(s) 210 and the sequences obtained from the protein sequence data 212, the challenging component 206 can generate a classification output 214 that indicates an amount of similarity and/or an amount of difference between the generated sequence 210 and sequences included in the protein sequence data 212. In one or more examples, the challenging component 206 can label the generated sequence(s) 210 as zero and the sequences obtained from the protein sequence data 212 as can be labeled as one. In these situations, the classification output 214 can correspond to a number from 0 and 1. In additional examples, the challenging component 206 can implement a distance function that produces an output that indicates an amount of distance between the generated sequence(s) 210 and the proteins included in the protein sequence data 212. In these scenarios, the challenging component 206 can label the generated sequence(s) 210 as −1 and the encoded amino acid sequences obtained from the protein sequence data 212 as 1. In implementations where the challenging component 206 implements a distance function, the classification output 214 can be a number from −∞ to ∞. In various examples, the amino acid sequences obtained from the protein sequence data 212 can be referred to as ground truth data.

The protein sequences included in the protein sequence data 212 can be subject to data preprocessing 216 before being provided to the challenging component 206. In one or more implementations, the protein sequence data 212 can be arranged according to a classification system before being provided to the challenging component 206. The data preprocessing 216 can include pairing amino acids included in the proteins of the protein sequence data 212 with numerical values that can represent structure-based positions within the proteins. The numerical values can include a sequence of numbers having a starting point and an ending point. In an illustrative example, a T can be paired with the number 43 indicating that a Threonine molecule is located at a structure-based position 43 of a specified protein domain type. In one or more illustrative examples, structure-based numbering can be applied to any general protein type, such as fibronectin type III (FNIII) proteins, avimers, antibodies, VHH domains, kinases, zinc fingers, and the like.

In one or more implementations, the classification system implemented by the data preprocessing 216 can designate a particular number of positions for certain regions of proteins. For example, the classification system can designate that portions of proteins having particular functions and/or characteristics can have a specified number of positions. In various situations, not all of the positions included in the classification system may be associated with an amino acid because the number of amino acids in a specified region of a protein may vary between proteins. To illustrate, the number of amino acids in a region of a protein can vary for different types of proteins. In one or more examples, positions of the classification system that are not associated with a particular amino acid can indicate various structural features of a protein, such as a turn or a loop. In an illustrative example, a classification system for antibodies can indicate that heavy chain regions, light chain regions, and hinge regions have a specified number of positions assigned to them and the amino acids of the antibodies can be assigned to the positions according to the classification system.

The data used to train the generative adversarial network architecture 202 can impact the amino acid sequences produced by the generating component 204. For example, in situations where antibodies are included in the protein sequence data 212 provided to the challenging component 206, the amino acid sequences generated by the generating component 204 can correspond to antibody amino acid sequences. In another example, in scenarios where T-cell receptors are included in the protein sequence data 212 provided to the challenging component 206 the amino acid sequences generated by the generating component 204 can correspond to T-cell receptor amino acid sequences. In one or more additional examples, in situations where kinases are included in the protein sequence data 212 provided to the challenging component 206, the amino acid sequences generated by the generating component 204 can correspond to amino acid sequences of kinases. In implementations where amino acid sequences of a variety of different types of proteins are included in the protein sequence data 212 provided to the challenging component 206, the generating component 204 can generate amino acid sequences having characteristics of proteins generally and may not correspond to a particular type of protein.

The output produced by the data preprocessing 216 can include structured sequences 218. The structured sequences 218 can include a matrix indicating amino acids associated with various positions of a protein. In one or more examples, the structured sequences 218 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The generated sequence(s) 210 can also be represented using a vector according to a same or similar number scheme as used for the structured sequences 218. In one or more illustrative examples, the structured sequences 218 and the generated sequence(s) 210 can be encoded using a method that may be referred to as a one-hot encoding method.

After the generative adversarial network architecture 202 has undergone a training process, one or more trained generating components 220 can be generated that can produce amino acid sequences of proteins. In one or more examples, the training process for the generative adversarial network architecture 202 can be complete after the function(s) implemented by the generating component 204 and the function(s) implemented by the challenging component 206 converge. The convergence of a function can be based on the movement of values of model parameters toward specified values as protein sequences are generated by the generating component 204 and feedback is obtained from the challenging component 206. In various implementations, the training of the generative adversarial network architecture 202 can be complete when the protein sequences generated by the generating component 204 have one or more specified characteristics. To illustrate, the amino acid sequences generated by the generating component 204 can be analyzed by a software tool that can analyze amino acid sequences to determine at least one of biophysical properties of the amino acid sequences, structural features of the amino acid sequences, or adherence to amino acid sequences corresponding to one or more protein germlines.

The one or more trained generating components 220 can included in an autoencoder training process 222. The autoencoder training process 222 can be implemented to train an autoencoder 224 to generate amino acid sequences of proteins. The autoencoder 224 can include an encoding component 226 and a decoding component 228. The decoding component 228 can include the one or more trained generating components 220. The encoding component 226 can produce code data 230 that is a representation of input obtained by the encoding component 226. The decoding component 228 can generate output that corresponds to the input obtained by the encoding component 226 based on the code data 230.

The autoencoder training process 222 can be implemented such that output generated by the decoding component 228 based on the code data 230 is analyzed with respect to the input obtained by the encoding component 226. During the autoencoder training process 222, the input data obtained by the encoding component 226 can include training data. In one or more examples, the training data can include amino acid sequences produced by the one or more trained generating components 220. The autoencoder training process 222 can be performed until the output produced by the decoding component 228 based on the code data 230 has at least a threshold amount of correspondence with the input obtained by the encoding component 226. In one or more illustrative examples, the threshold amount of correspondence between the output produced by the decoding component 228 and the input obtained by the encoding component 226 can be related to an amount of similarity between amino acid sequences generated by the decoding component 228 and amino acid sequences of training data obtained by the encoding component 226. The amount of similarity between amino acid sequences generated by the decoding component 228 and amino acid sequences of training data obtained by the encoding component 226 can indicate an amount of identity between the input sequences obtained by the encoding component 226 and the output sequences produced by the decoding component 228.

The autoencoder training process 222 can produce a trained autoencoder 232. Although previous implementations of autoencoders include an encoding component having a number of computational layers that are mirrored in the decoding component, in implementations described herein, the trained autoencoder 232 can include an encoder and a decoder that have computational layers that are not mirrors with respect to one another. The trained autoencoder 232 can obtain one or more base sequences 234 and produce one or more variant sequences 236 based on the one or more base sequences 234. A base sequence 234 can include an amino acid sequence of a base protein and the one or more variant sequences 236 can include amino acid sequences of variant proteins that differ in at least one position from the base protein. In various examples, the trained autoencoder 232 can include a trained encoding component that produces code data based on a base sequence 234 and the code data can be utilized by a decoding component of the trained autoencoder 232 to produce the one or more variant sequences 236.

Figure 3:
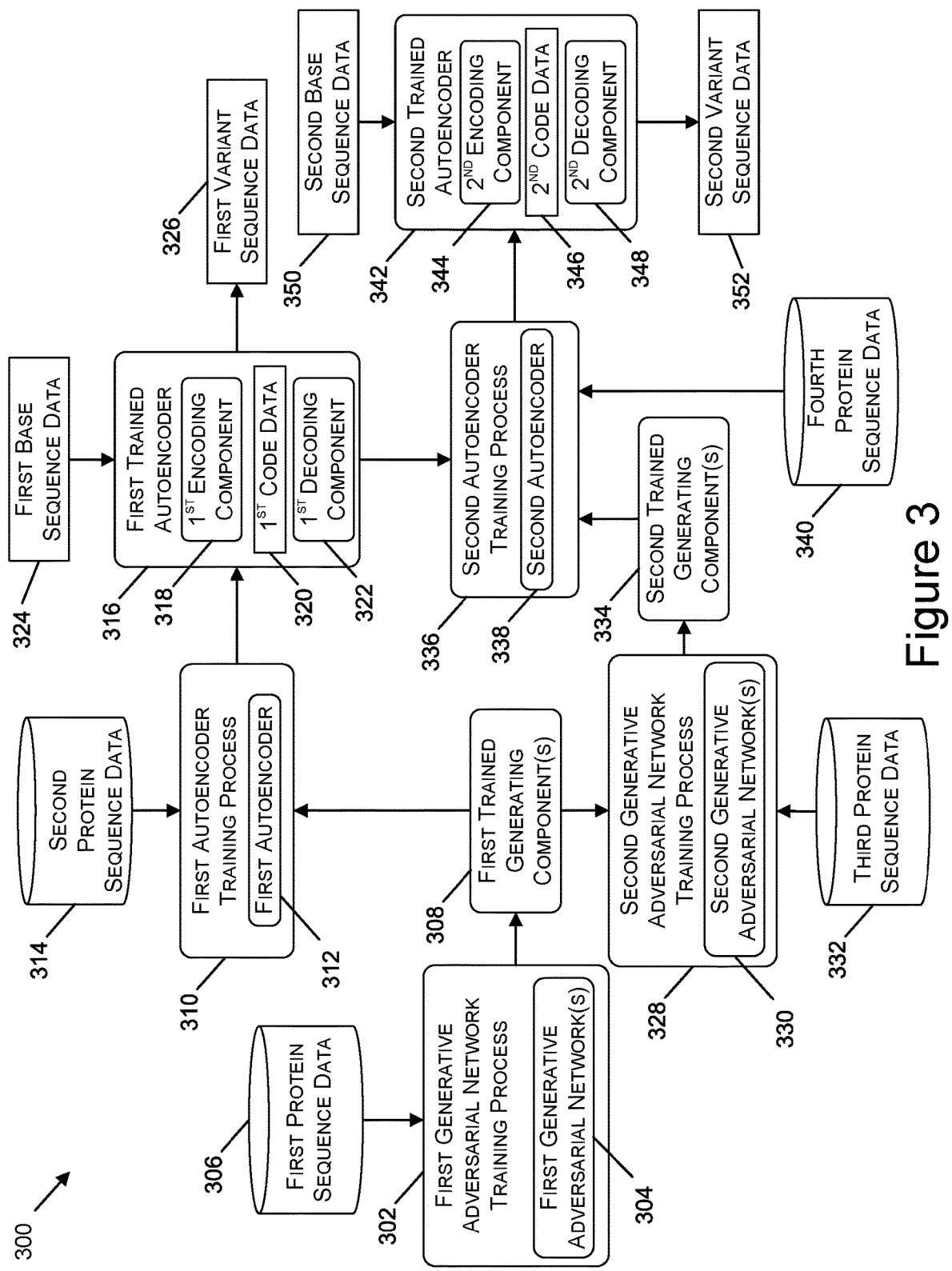
FIG. 3 is a diagram illustrating an example framework to perform transfer learning with respect to a first generative adversarial network and produce a second generative adversarial network that can be used as a decoding component of an autoencoder, in accordance with some implementations.

FIG. 3 is a diagram illustrating an example framework 300 to perform transfer learning with respect to a first generative adversarial network and produce a second generative adversarial network that can be used as a decoding component of an autoencoder, in accordance with some implementations. By implementing transfer learning techniques with respect to generative adversarial networks that operate as decoding components of autoencoders, amino acid sequences of variant proteins can be produced based on at least one amino acid sequence of a base protein, where the variant proteins have one or more specified structural features and/or one or more specified biophysical properties.

The framework 300 can include a first generative adversarial network training process 302. The first generative adversarial network training process 302 can include training one or more first generative adversarial networks 304 to produce amino acid sequences of proteins. The one or more first generative adversarial networks 304 can include one or more generating components and one or more challenging components. In one or more examples, the first generative adversarial network training process 302 can include training a first generative adversarial network 304 to produce amino acid sequences of antibodies. The one or more challenging components can analyze amino acid sequences produced by the one or more generating components with respect to training data that includes a number of amino acid sequences of proteins. For example, the first generative adversarial network training process 302 can train the one or more first generative adversarial networks 304 based on first protein sequence data 306. The first protein sequence data 306 can include amino acid sequences of a number of proteins obtained from one or more data sources and stored in one or more databases that are accessible to the one or more first generative adversarial networks 304. The first generative adversarial network training process 302 can proceed until one or more criteria have been satisfied. The one or more criteria can indicate one or more characteristics of proteins that correspond to amino acid sequences of proteins produced by the one or more first generative adversarial networks 304. The one or more criteria can also be related to the convergence of one or more functions implemented by the one or more first generative adversarial networks 304. In various examples, the amino acid sequences produced by a first generative adversarial network 304 that has undergone the first generative adversarial network training process 302 can have one or more structural features and/or one or more biophysical properties that correspond to at least a portion of the structural features and/or at least a portion of the biophysical properties of the proteins that correspond to the amino acid sequences included in the first protein sequence data 306.

After training one or more first generative adversarial networks 304 according to the first generative adversarial network training process 302, one or more first trained generating components 308 can be produced that generate amino acid sequences of proteins. The one or more first trained generating components 308 can be used in a first autoencoder training process 310. The first autoencoder training process 310 can train a first autoencoder 312. The first autoencoder 312 can include an encoding component and a decoding component. The decoding component can comprise a first trained generating component 308. The first autoencoder 312 can be trained using second protein sequence data 314. The second protein sequence data 314 can include amino acid sequences of proteins that have been obtained from one or more data sources. In one or more examples, the second protein sequence data 314 can include amino acid sequences generated by a first trained generating component 308. In one or more illustrative examples, during the first autoencoder training process 310, amino acid sequences included in the second protein sequence data 314 can be obtained by an encoding component of the first autoencoder 312 and the encoding component can generate code data that corresponds to a representation of the input amino acid sequences. The decoding component of the first autoencoder 312 can generate an output amino acid sequence based on the representation produced by the encoding component. The first autoencoder training process 310 can proceed until one or more criteria for training the first autoencoder 312 have been satisfied. The one or more criteria used to determine when to stop the first autoencoder training process 310 can be related to measures of similarity between the amino acid sequences providing as training data from the second protein sequence data 314 and the amino acid sequences produced by the decoding component of the first autoencoder 312 based on the code data generated by the encoding component of the first autoencoder 312.

The first autoencoder training process 310 can produce a first trained autoencoder 316. The first trained autoencoder 316 can include a first encoding component 318 that produces first code data 320. The first code data 320 can include a representation of data provided as input to the first encoding component 318. The first trained autoencoder 316 can also include a first decoding component 322. In one or more examples, the first decoding component 322 can include a first trained generating component 308. In various examples, computational layers of a first trained generating component 308 that is included in the first autoencoder 312 can remain unchanged during the first autoencoder training process 310. In these scenarios, the computational layers of the first decoding component 322 correspond to the computational layers of the first trained generating component 308 included in the first autoencoder 312.

In one or more implementations, the first trained autoencoder 316 can obtain first base sequence data 324. The first base sequence data 324 can correspond to amino acid sequences of one or more base proteins. The first trained autoencoder 316 can generate first variant sequence data 326 based on the first base sequence data 324. The first variant sequence data 326 can correspond to amino acid sequences of proteins that are variants of the base protein related to the first base sequence data 324. The variant proteins can have an amino acid in at least one position that is different from the amino acid in the same position of the base protein. In one or more illustrative examples, the first encoding component 318 can obtain the first base sequence data 324 and generate the first code data 320. In these situations, the first code data 320 can correspond to a representation of the first base sequence data 324. In various examples, the first code data 320 can correspond to a compressed version of the first base sequence data 324. The first decoding component 322 can generate the first variant sequence data 326 based on the first code data 320. In one or more examples, the first code data 320 can be modified and the modified version of the first code data 320 can be used by the first decoding component 322 to generate the first variant sequence data 326. In one or more additional examples, the first decoding component 322 can generate the first variant sequence data 326 directly from the first code data 320.

In addition to being included in the first autoencoder 312 and being part of the first autoencoder training process 310, the one or more first trained generating components 308 can also be included in a second generative adversarial network training process 328. The second generative adversarial network training process 328 can be used to train one or more second generative adversarial networks 330. The one or more second generative adversarial networks 330 can include a generating component that comprises a first trained generating component 308 and a challenging component. The one or more second generative adversarial networks 330 can be trained according to third protein sequence data 332. The third protein sequence data 332 can include amino acid sequences of a number of proteins. The number of proteins corresponding to the amino acid sequences of the third protein sequence data 332 can be different from the proteins corresponding to the amino acid sequences of the first protein sequence data 306 used in the first generative adversarial network training process 302. In one or more examples, the second generative adversarial network training process 328 can implement transfer learning techniques that modify the first trained generating components 308. By using a training dataset in the second generative adversarial network training process 328 that is different from the training dataset used in the first generative adversarial network training process 302, the one or more second generative adversarial networks 330 can produce amino acid sequences that can have some general characteristics that correspond to the amino acid sequences included in the first protein sequence data 306 and that also have one or more specified characteristics that correspond to features of the proteins related to the amino acid sequences included in the third protein sequence data 332.

In various implementations, the one or more first trained generating components 308 can be further trained using the third protein sequence data 332 as part of a transfer learning process to produce one or more second trained generating components 334 in a manner that is similar to the training of the one or more first generative adversarial networks 304 that produced the one or more first trained generating components 308. In one or more examples, components of the one or more second generative adversarial networks 330 can be trained to minimize at least one loss function. Additionally, the second generative adversarial network training process 328 used to produce the one or more second trained generating components 334 can be complete after one or more modified functions implemented by the one or more second generative adversarial networks 330 converge. In one or more further examples, the second generative adversarial network training process 328 can be complete based on an analysis of a software tool indicating that amino acid sequences produced using the one or more second generative adversarial networks 330 corresponds to one or more specified criteria. The one or more specified criteria can correspond to proteins associated with the amino acid sequences produced by the generating component of a second generative adversarial network 330 having at least one of one or more structural features of interest or one or more biophysical properties of interest.

In one or more examples, the third protein sequence data 332 can include amino acid sequences of proteins that have features that are different from the features of the proteins related to the first protein sequence data 306. In various examples, the third protein sequence data 332 can include a subset of the amino acid sequences included in the first protein sequence data 306. In additional examples, the third protein sequence data 332 can include a greater number of a group of amino acid sequences having one or more specified characteristics in relation to the number of amino acid sequences having the one or more characteristics included in the first protein sequence data 306. For example, the first protein sequence data 306 can include amino acid sequences of proteins having a variety of structural features. To illustrate, the first protein sequence data 306 can include a number of amino acid sequences of proteins having one or more sizes of hydrophobic regions, a number of amino acid sequences of proteins having one or more sizes of negatively charged regions, a number of amino acid sequences of proteins having one or more sizes of positively charged regions, a number of amino acid sequences of proteins one or more sizes of polar regions, one or more combinations thereof, and the like. In one or more implementations, the third protein sequence data 332 can include amino acid sequences of proteins that have a greater number of amino acid sequences of proteins having a subset of the properties of the proteins included in the first protein sequence data 306, such as a greater number of amino acid sequences of proteins that have hydrophobic regions with a specified range of sizes than the number of amino acid sequences included in the first protein sequence data 306 that have the hydrophobic regions with the specified range of sizes. In these scenarios, the one or more second trained generating components 334 can primarily produce amino acid sequences of proteins having hydrophobic regions with the specified range of sizes.

In one or more implementations, the amino acid sequences included in the third protein sequence data 332 can include a filtered set of amino acid sequences. For example, a set of amino acid sequences can be evaluated according to one or more criteria. In various examples, at least one of one or more software tools, one or more diagnostic tools, or one or more analytical instruments can be used to identify amino acid sequences included in the set of amino acid sequences that correspond to the one or more criteria. The amino acid sequences that satisfy the one or more criteria can then be added to the third protein sequence data 332. In one or more illustrative examples, a number of amino acid sequences can be evaluated to identify proteins having at least one polar region for inclusion in the third protein sequence data 332. In these scenarios, the amino acid sequences that include at least one polar region can be used to modify the one or more first trained generating components 308 during the second generative adversarial network training process 328 to produce the one or more second trained generating components 334 that have at least a threshold probability of generating amino acid sequences of proteins having at least one polar region.

The first trained autoencoder 316 and the one or more second trained generating components 334 can be used in a second autoencoder training process 336. The second autoencoder training process 336 can train a second autoencoder 338 that includes the first encoding component 318 and a decoding component that comprises a second trained generating component 334. The second autoencoder 338 can be trained using fourth protein sequence data 340. The fourth protein sequence data 340 can include amino acid sequences of proteins that have been obtained from one or more data sources. In one or more examples, the fourth protein sequence data 340 can include amino acid sequences generated by at least one of the second trained generating components 334.

In one or more implementations, during the second autoencoder training process 336, amino acid sequences included in the fourth protein sequence data 340 can be obtained by an encoding component of the second autoencoder 338, such as the first encoding component 318, and the encoding component can generate code data that corresponds to a representation of the input amino acid sequences. The decoding component of the second autoencoder 338, such as a second trained generating component 334, can generate an output amino acid sequence based on the representation produced by the encoding component. The second autoencoder training process 336 can proceed until one or more criteria for training the second autoencoder 338 have been satisfied. The one or more criteria used to determine when to stop the second autoencoder training process 336 can be related to measures of similarity between the amino acid sequences providing as training data from the fourth protein sequence data 340 and the amino acid sequences produced by the decoding component of the second autoencoder 338 based on the code data generated by the encoding component of the second autoencoder 338.

The second autoencoder training process 336 can produce a second trained autoencoder 342. The second trained autoencoder 342 can include a second encoding component 344 that produces second code data 346. The second code data 346 can include a representation of data obtained as input to the second encoding component 344. The second trained autoencoder 342 can also include a second decoding component 348. In one or more examples, the second decoding component 348 can include a second trained generating component 334. In various examples, computational layers of a second trained generating component 334 that is included in the second autoencoder 338 can remain unchanged during the second autoencoder training process 336. In these scenarios, the computational layers of the second decoding component 348 can correspond to the computational layers of the second trained generating component 334 included in the second autoencoder 338.

In one or more implementations, the second trained autoencoder 342 can obtain second base sequence data 350. The second base sequence data 350 can correspond to amino acid sequences of one or more base proteins. The second trained autoencoder 342 can generate second variant sequence data 352 based on the second base sequence data 350. The second variant sequence data 352 can correspond to amino acid sequences of proteins that are variants of the base protein related to the second base sequence data 350. The variant proteins can have an amino acid in at least one position that is different from the amino acid in the same position of the base protein. In one or more illustrative examples, the second encoding component 344 can obtain the second base sequence data 350 and generate the second code data 346. In these situations, the second code data 346 can correspond to a representation of the second base sequence data 350. In various examples, the second code data 346 can correspond to a compressed version of the second base sequence data 350. The second decoding component 348 can generate the second variant sequence data 352 based on the second code data 346. In one or more examples, the second code data 346 can be modified and the modified version of the second code data 346 can be used by the second decoding component 348 to generate the second variant sequence data 352. In one or more additional examples, the second decoding component 348 can generate the second variant sequence data 352 directly from the second code data 346.

As a result of using at least one second trained generating component 334 as the second decoding component 348, the variant proteins that correspond to the second variant sequence data 352 can have characteristics that correspond to those of the proteins related to the amino acid sequences included in the third protein sequence data 332. That is, by performing a second generative adversarial network training process 328 using training data that corresponds to proteins have one or more structural features of interest and/or one or more biophysical properties of interest, the variant proteins that correspond to the amino acid sequences of the second variant sequence data 352 can also have at least a threshold probability of having the one or more structural features of interest and/or the one or more biophysical properties of interest. Thus, the framework 400 can be implemented in scenarios where variant proteins of a base protein are to be produced that have one or more structural features of interest and/or one or more biophysical properties of interest. Additionally, by leveraging the learning that takes place to produce the one or more first trained generating components 308 followed by the transfer learning using a more specialized training dataset with respect to the second generative adversarial network training process 328, the computing resources used to generate the second variant sequence data 352 can be minimized and the accuracy of the characteristics of interest for the variant proteins can be increased in relation to previous techniques.

Further, although a single additional generative adversarial network training process (e.g., the second generative adversarial network training process 328) and a single additional autoencoder training process (e.g., the second autoencoder training process 336) are described with respect to the illustrative example of FIG. 3, multiple additional training processes for the generative adversarial networks and autoencoders can be performed. In one or more examples, the multiple structural features and/or multiple biophysical properties can be of interest with respect to variant proteins of a base protein. In these scenarios, an additional training dataset that includes amino acid sequences of one or more of the structural features and/or biophysical properties of interest can be used in one or more additional transfer learning processes to further train the generating components of the generative adversarial networks. Modifications to the generating components of the generative adversarial networks can result in modifications to the encoding components and decoding components of the autoencoders. Thus, with each additional training process and subsequent modifications to the computational layers of the generative adversarial network generating components that operate as the decoding components for the autoencoders and the modifications to the encoding components, the characteristics of the proteins corresponding to the amino acid sequences generated by the trained autoencoders can be further modified.

Additionally, although the illustrative example of FIG. 3 indicates the implementation of transfer learning techniques by training the generating components of one or more generative adversarial networks with different datasets, transfer learning techniques can be implemented to produce a second trained autoencoder from a first trained autoencoder by using a training dataset for the second autoencoder training process that is not produced by a generating component that has undergone a transfer learning process. For example, performing a transfer learning process to generate the second trained generating components 334 using the first trained generating components 308 can be absent from the framework 300. In these situations, the first trained autoencoder 316 can be part of the second autoencoder training process 336. Continuing with this example, an additional dataset, such as the third protein sequence data 332, can be used as training data for the second autoencoder training process 336. Also in these scenarios, the second autoencoder training process 336 can be different from the first autoencoder training process 310 because the computational layers of the first decoding component 322 may not be held constant during the second autoencoder training process 336. Thus, the computational layers of the first encoding component 318 and the computational layers of the first decoding component 322 can both be modified during the second autoencoder training process 336.

Figure 4:
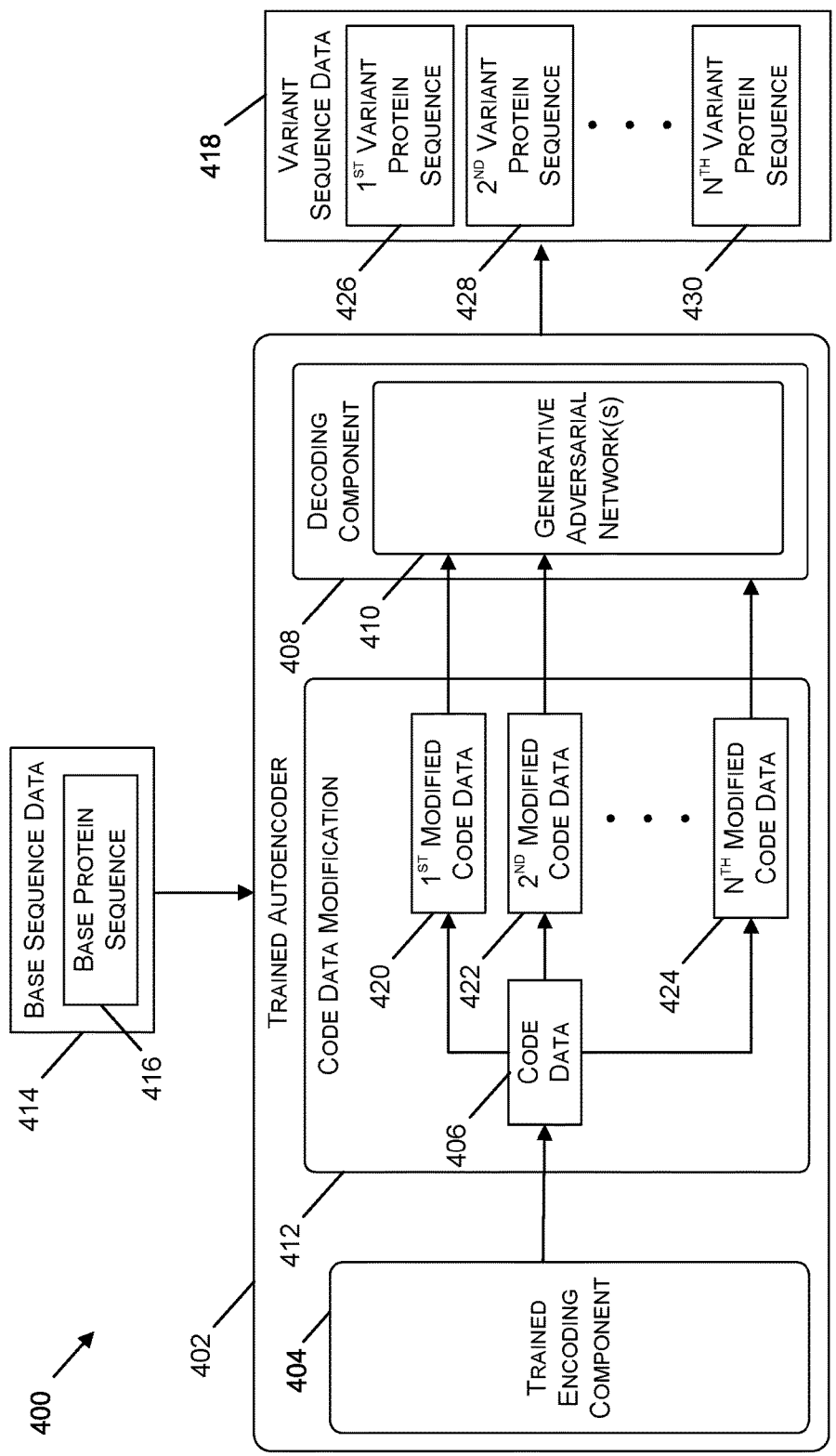
FIG. 4 is a diagram illustrating an example framework to modify code data produced by an encoding component of an autoencoder to generate amino acid sequences of variants of a base protein, in accordance with some implementations.

FIG. 4 is a diagram illustrating an example framework 400 to modify code data produced by an encoding component of an autoencoder to generate amino acid sequences of variants of a base protein, in accordance with some implementations. The framework 400 can include a trained autoencoder 402. The trained autoencoder 402 can be produced using one or more implementations of autoencoder training processes described in relation to at least one of FIG. 1, FIG. 2, or FIG. 3. The trained autoencoder 402 can be implemented using at least one of computer-readable instructions, logic, or circuitry.

The trained autoencoder 402 can include a trained encoding component 404 that can produce code data 406 based on input obtained by the trained encoding component 404. The code data 406 can include a representation of the input obtained by the trained encoding component 404. The code data 406 can be produced by a number of computational layers of the trained encoding component 404 based on input obtained by the trained encoding component 404. In one or more examples, the code data 406 can include a compressed representation of the input obtained by the trained encoding component 404. The compressed representation corresponding to the code data 406 can include less data than the input obtained by the trained encoding component 404.

The trained autoencoder 402 can also include a decoding component 408 The decoding component 408 can generate output based on the code data 406. In one or more examples, the output generated by the decoding component 408 based on the code data 406 can have at least a threshold measure of similarity with respect to input obtained by the trained encoding component 404. In the illustrative example of FIG. 4, the decoding component 408 can include one or more components of one or more generative adversarial networks 410. In various examples, the decoding component 408 can include one or more generating components of the one or more generative adversarial networks 410.

The trained autoencoder 402 can perform code data modification 412. The code data modification 412 can include modifying one or more features of the code data 406 and providing the modified code data to the decoding component 408. In these scenarios, the output produced by the decoding component 408 can be based on an extent of the modifications made to the code data 406. For example, as the modifications to the code data 406 increase, differences between input obtained by the trained encoding component 404 and output generated by the decoding component 408 can also increase.

In one or more implementations, the code data 406 can include a number of numerical values. In various examples, the numerical values can be included in a range of values. To illustrative, numerical values of the code data 406 can be included in a range from −1 to 1. In one or more additional examples, the numerical values of the code data 406 can include floating point numbers. In one or more illustrative examples, the code data 406 can include a matrix of numerical values. For example, the code data 406 can include a 1×296 matrix. In situations where the code data 406 includes a number of numerical values, modifying one or more features of the code data 406 can include modifying one or more numerical values of the code data 406. Modifications to numerical values of the code data 406 can include modifying a number of the numerical values. Additionally, modifications to the numerical values of the code data 406 can include modifying respective magnitudes of the individual numerical values. In one or more instances, an extent of modification of the code data 406 can include at least one of a number of numerical values of the code data 406 that are modified or a magnitude that individual numerical values of the code data 406 are modified.

Input to the trained autoencoder 402 can include base sequence data 414 that corresponds to one or more amino acid sequences of base proteins, such as a base protein sequence 416. The trained encoding component 404 can produce code data 406 that corresponds to a representation of the base sequence data 414. For example, the trained encoding component 404 can generate code data 406 that is a representation of the base protein sequence 416 and includes less data than the base sequence data 414. Code data modification 412 can take place that modifies one or more numerical values of the code data 406 to produce modified code data. The modified code data can be provided to the decoding component 408 to produce output that corresponds to amino acid sequences of variants of the base protein sequence 416.

The output of the decoding component 408 based on one or more modified versions of the code data 406 can include variant sequence data 418. The code data modification 412 can include modifying a number of the numerical values of the code data 406 by a respective amount. Individual numerical values of the code data 406 can be modified by different amounts. In one or more additional examples, individual numerical values of the code data 406 can be modified by a same amount. In the illustrative example of FIG. 4, the code data modification 412 can include producing first modified code data 420, second modified code data 422, up to Nth modified code data 424. The first modified code data 420 can include first modifications to numerical values of the code data 406, the second modified code data 422 can include second modifications to numerical values of the code data 406, and the Nth modified code data 424 can include Nth modifications to numerical values of the code data 406. The first modifications used to produce the first modified code data 420 can include first modifications to a number of numerical values of the code data 406 that are different from the second modifications of the numerical values of the code data 406 used to generate the second modified code data 422 and different from the Nth modifications to numerical values of the code data 406 to produce the Nth modified code data 424. Additionally, the second modifications made to the code data 406 to produce the second modified code data 422 can be different from the Nth modifications made to the code data 406 to generate the Nth modified code data 424.

The differences between the first modified code data 420, the second modified code data 422, and the Nth modified code data 424 can be related to the number of numerical values of the code data 406 modified with respect to the first modified code data 420, the second modified code data 422, and the Nth modified code data 424. For example, a first number of numerical values of the code data 406 can be modified to produce the first modified code data 420 and a second number of numerical values of the code data 406 can be modified to produce the second modified code data 422, where the second number of numerical values is different from the first number of numerical values. Further, a third number of numerical values of the code data 406 can be modified to produce the Nth modified code data 424 that is different from the first number of numerical values and the second number of numerical values.

In one or more additional examples, the differences between the first modified code data 420, the second modified code data 422, and the Nth modified code data 424 can be related to the magnitude of changes to the numerical values of the code data 406 with respect to the first modified code data 420, the second modified code data 422, and the Nth modified code data 424. The magnitude of changes to a numerical value of the code data 406 can correspond to a difference between an initial numerical value and a modified numerical value. The magnitude of changes to the numerical values of the code data 406 that produce the first modified code data 420 can be different from the magnitude of changes to the numerical values of the code data 406 used to produce the second modified code data 422 and can be different from the magnitude of changes to the numerical values of the code data 406 that produce the Nth modified code data 424. Additionally, the magnitude of changes to the numerical values of the code data 406 to produce the second modified code data 422 can be different from the magnitude of changes to the numerical values of the code data 406 to produce the Nth modified code data 424. The magnitude of changes to numerical values of the code data 406 can correspond to at least one of a sum of magnitude changes to numerical values of the code data 406, an absolute value of the sum of magnitude changes to numerical values of the code data 406, an average value of magnitude changes to numerical values of the code data 406, or magnitude changes to one or more individual numerical values of the code data 406.

The variant sequence data 418 generated by the decoding component 408 can include a first variant protein sequence 426, a second variant protein sequence 428, up to an Nth variant protein sequence 430. The decoding component 408 can generate the first variant protein sequence 426 based on the first modified code data 420 and the decoding component 408 can generate the second variant protein sequence 428 based on the second modified code data 422. In addition, the decoding component 408 can generate the Nth variant protein sequence 430 based on the Nth modified code data 424. The first variant protein sequence 426 can include a first number of differences between initial amino acids located at one or more first positions of the base protein sequence 416 and first modified amino acids located at the one or more first positions of the first variant protein sequence 426. The second variant protein sequence 428 can include a second number of differences between initial amino acids located at one or more second positions of the base protein sequence 416 and second modified amino acids located at the one or more second positions of the second variant protein sequence 428. In addition, the Nth variant protein sequence 430 can include a third number of differences between initial amino acids located at one or more third positions of the base protein sequence 416 and third modified amino acids located at the one or more third positions of the Nth variant protein sequence 430.

The differences between the base protein sequence 416 and the first variant protein sequence 426 can be based on differences between the code data 406 and the first modified code data 420. Additionally, differences between the base protein sequence 416 and the second variant protein sequence 428 can be based on differences between the code data 406 and the second modified code data 422. Further, differences between the base protein sequence 416 and the Nth variant protein sequence 430 can be based on differences between the code data 406 and the Nth modified code data 424. In one or more examples, a first amount of differences between numerical values of the code data 406 and the first modified code data 420 can correspond to first differences of amino acids at a first number of positions of the base protein sequence 416 in relation to amino acids at the first number of positions of the first variant protein sequence 426. In one or more additional examples, a second amount of differences between numerical values of the code data 406 and the second modified code data 422 can correspond to second differences of amino acids at a second number of positions of the base protein sequence 416 in relation to amino acids at the second number of positions of the second variant protein sequence 428. In one or more illustrative examples, the first amount of differences between the numerical values of the code data 406 and the first modified code data 420 can be greater than the second amount of differences between the numerical values of the code data 406 and the second modified code data 422. In these scenarios, the first differences of amino acids at the first number of positions of the base protein sequence 416 in relation to the amino acids at the first number of positions of the first variant protein sequence 426 can be greater than the second differences of amino acids at the second number of positions of the base protein sequence 416 in relation to the amino acids at the second number of positions of the second variant protein sequence 428. The first amount of differences between the code data 406 and the first modified code data 420 can be greater than the second amount of differences between the code data 406 and the second modified code data 422 based on a number of numerical values of the code data 406 that have been changed with respect to the first modified code data 420 and the second modified code data 422 and/or a magnitude of changes to one or more numerical values of the code data 406 with respect to the first modified code data 420 and the second modified code data 422.

In one or more examples, the base protein sequence 416 and the variant protein sequences 426, 428, 430 can include at least a portion of an amino acid sequence of a base protein. In one or more illustrative examples, the base protein sequence 416 and the variant protein sequences 426, 428, 430 can include an amino acid sequence of at least a portion of an antibody. For example, the base protein sequence 416 and the variant protein sequences 426, 428, 430 can include at least a portion of a heavy chain of an antibody or at least a portion of a light chain of an antibody. In one or more additional examples, the base protein sequence 416 and the variant protein sequences 426, 428, 430 can include at least a portion of a variable region of a light chain or at least a portion of a variable region of a heavy chain of an antibody. The base protein sequence 416 and the variant protein sequences 426, 428, 430 can also include at least a portion of a constant region of a light chain or at least a portion of a constant region of a heavy chain of an antibody. In one or more further illustrative examples, the base protein sequence 416 and the variant protein sequences 426, 428, 430 can include at least a portion of a complementarity determining region (CDR) of an antibody. In situations where the base protein sequence 416 and the variant protein sequences 426, 428, 430 include a portion of a sequence of a protein, additional amino acids can subsequently be added to the variant protein sequences 426, 428, 430. To illustrate, in scenarios where the variant protein sequences 426, 428, 430 are amino acid sequences of at least a portion of a CDR of an antibody, additional amino acids can be added to the variant protein sequences 426, 428, 430 to produce one or more portions of an antibody sequence, such as a heavy chain or a light chain of an antibody, or to produce a greater amount of antibody sequences that include one or more heavy chains, one or more light chains, and one or more hinge regions.

Figure 5:
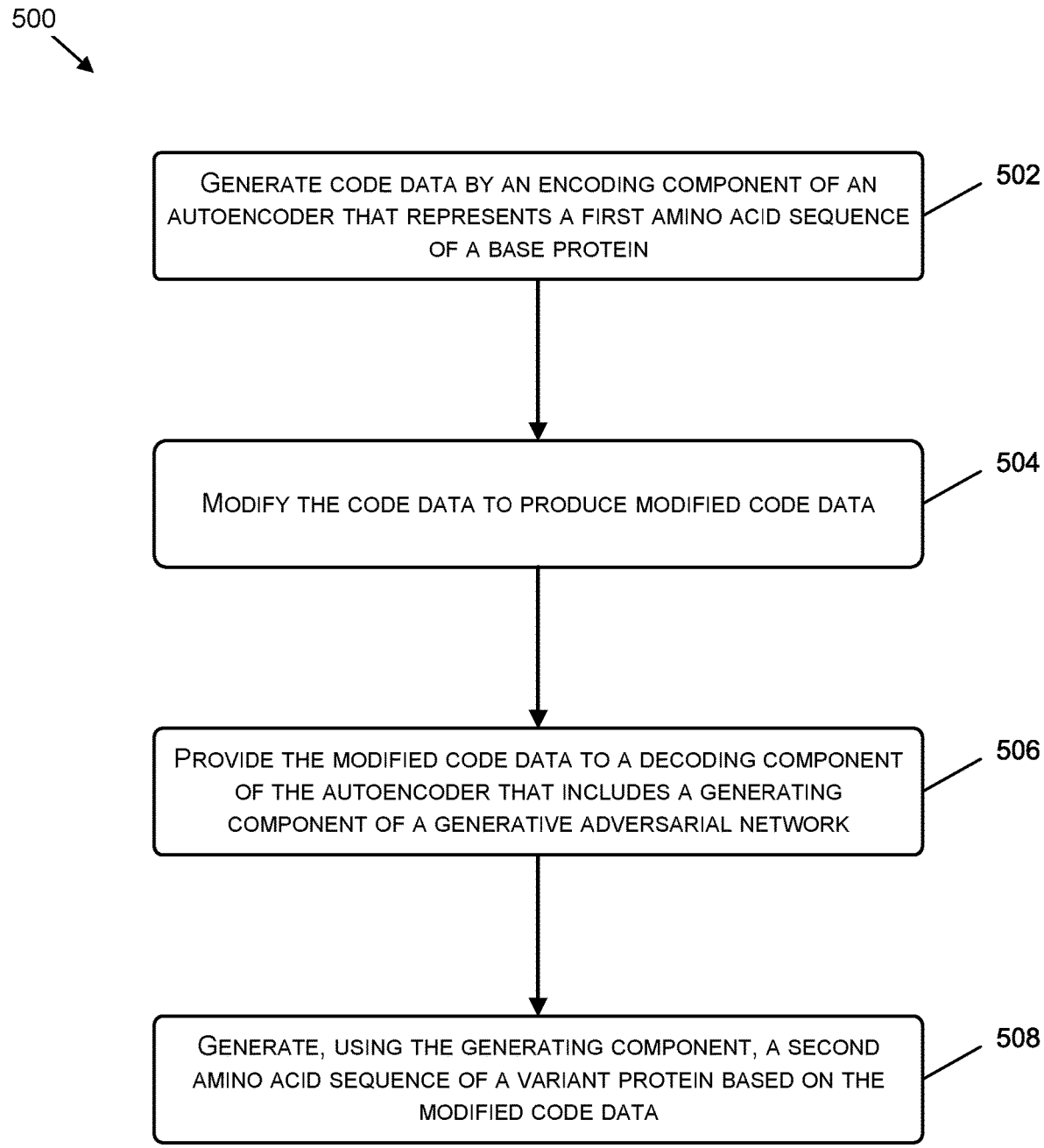
FIG. 5 is a flow diagram illustrating an example process to modify code data produced by an encoding component of an autoencoder to produce amino acid sequences of variants of a base protein using one or more components of a generative adversarial network as a decoding component of the autoencoder, in accordance with some implementations.
Figure 6:
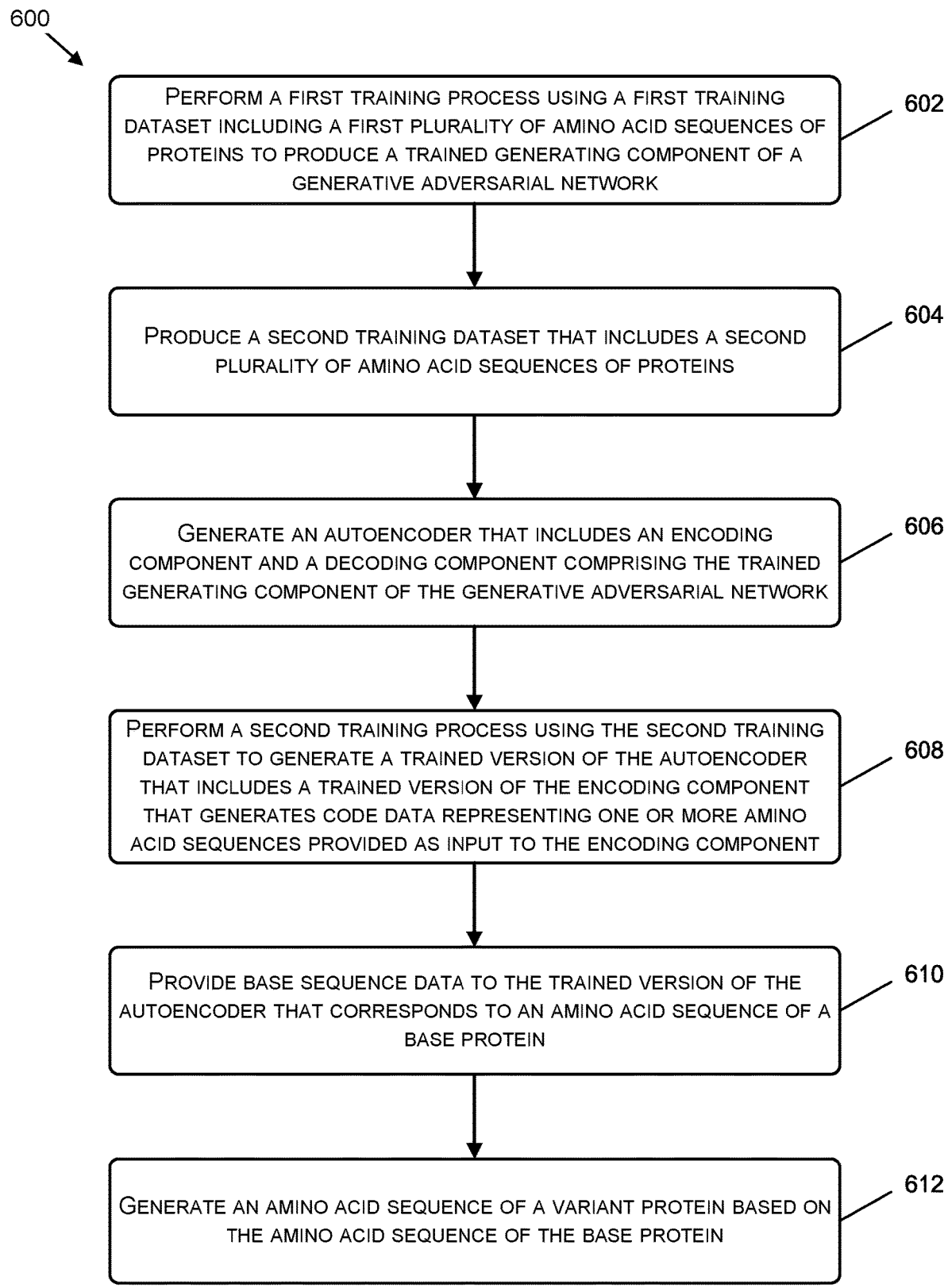
FIG. 6 is a flow diagram illustrating an example process to generate an autoencoder that produces amino acid sequences of variants using one or more components of a generative adversarial network as a decoding component of the autoencoder, in accordance with some implementations, in accordance with some implementations.

FIGS. 5 and 6 illustrate example processes for generating amino acid sequences of proteins using machine learning techniques. The example processes are illustrated as collections of blocks in logical flow graphs, which represent sequences of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular data types. The order in which the operations are described is not intended to be construed as a limitation, and any number of the described blocks can be combined in any order and/or in parallel to implement the process.

FIG. 5 is a flow diagram illustrating an example process 500 to modify code data produced by an encoding component of an autoencoder to produce amino acid sequences of variants of a base protein using one or more components of a generative adversarial network as a decoding component of the autoencoder, in accordance with some implementations. The process 500 can include, at 502, generating code data by an encoding component of an autoencoder that represents a first amino acid sequence of a base protein. The code data can correspond to a representation of the first amino acid sequence. In one or more examples, the code data can include a plurality of numerical values. In one or more illustrative examples, the code data can include a 1×296 matrix.

In addition, the process 500 can include, at 504, modifying the code data to produce modified code data. The code data can be modified by modifying one or more numerical values of the code data. In various examples, the numerical values of the code data can be modified by changing by increasing or decreasing a respective numerical value by an amount. At 506, the process 500 can include providing the modified code data to a decoding component of the autoencoder. The decoding component can include a generating component of a generative adversarial network.

Further, at 508, the process 500 can include generating, using the generating component, a second amino acid sequence of a variant protein based on the modified code data. In one or more examples, the second amino acid sequence of the variant protein can include a same number of amino acids as the first amino acid sequence of the base protein and have one or more modifications of an amino acid at one or more positions with respect to the amino acids of the first sequence of the base protein at the same one or more positions. In one or more additional examples, the second amino acid sequence of the variant protein can have a different number of amino acids than the first amino acid sequence of the base protein. In various examples, the second amino acid sequence of the variant protein can have at least a threshold amount of sequence identity with the first amino acid sequence of the base protein. The amount of differences between the first amino acid sequence of the base protein and the second amino acid sequence of the variant protein can be based on a number of modifications made to the modified code data with respect to the code data.

In one or more examples, an initial version of the generating component can be previously trained to generate amino acid sequences of proteins that have one or more structural features of interest and/or one or more biophysical properties of interest. In these scenarios, the generating component can be previously trained to produce amino acid sequences having a first amount of amino acid sequences that correspond to proteins having the one or more structural features of interest and/or the one or more biophysical properties of interest. The generating component can be further trained using different training data to produce amino acid sequences having a second amount of amino acid sequences that correspond to proteins having the one or more structural features of interest and/or the one or more biophysical properties of interest. Accordingly, the version of the generating component that has been further trained using different training data can produce a number of amino acid sequences that has a greater proportion of amino acid sequences of proteins that correspond to the one or more structural features of interest and/or the one or more biophysical properties of interest than the proteins corresponding to the amino acid sequences produced by the previous version of the generating component. In various examples, the probability that the further trained version of the generating component generates amino acid sequences of proteins having the one or more structural features of interest and/or the one or more biophysical properties of interest can be greater than a probability that the initial version of the generating component can generate amino acid sequences of proteins having the one or more structural features of interest and/or the one or more biophysical properties of interest.

Additionally, an autoencoder that includes a further trained version of the generating component can have a greater probability of producing amino acid sequences having the one or more structural features of interest and/or the one or more biophysical properties of interest than an autoencoder that includes an initial version of the generating component. In one or more examples, an autoencoder that includes a further trained version of the generating component can produce a higher proportion of amino acid sequences corresponding to proteins having the one or more structural features of interest and/or the one or more biophysical properties of interest than an autoencoder that includes an initial version of the generating component.

FIG. 6 is a flow diagram illustrating an example process 600 to generate an autoencoder that produces amino acid sequences of variants using one or more components of a generative adversarial network as a decoding component of the autoencoder, in accordance with some implementations. At 602, the process 600 can include performing a first training process using a first training dataset including a first plurality of amino acids sequences of proteins to produce a trained generating component of a generative adversarial network. The first training process can produce a trained generating component that produces amino acid sequences of proteins having a first group of one or more structural features and/or a first group of one or more biophysical properties. The first group of one or more structural features and/or the first group of one or more biophysical properties can correspond to characteristics of the proteins associated with the plurality of first amino acid sequences included in the first training dataset.

The process 600 can also include, at 604, producing a second training dataset that includes a second plurality of amino acid sequences of proteins. In one or more examples, the second training dataset can be produced using the trained generating component. In addition, at 606, the process 600 can include generating an autoencoder that includes an encoding component and a decoding component. The decoding component can comprise the trained generating component of the generative adversarial network. At 608, the process 600 can include performing a second training process using the second training dataset to generate a trained version of the autoencoder. The trained version of the autoencoder can include a trained version of the encoding component and the decoding component of the trained version of the autoencoder can include the trained generating component. During the training process, the computational layers of the encoding component can be modified based on differences between the amino acid sequences included in the second training dataset and the amino acid sequences produced by the decoding component. The differences between the amino acid sequences included in the second training dataset and the amino acid sequences produced by the decoding component can correspond to a measure of identity between the amino acid sequences included in the second training dataset in relation to respective amino acid sequences produced by the decoding component. In various examples, the computational layers of the decoding component can be held constant during the second training process. The encoding component of the trained version of the autoencoder can produce code data based on input obtained by the encoding component. The code data can include a representation of the input obtained by the encoding component. In addition, the decoding component can produce output based on the code data.

Further, at 610, the process 600 can include providing base sequence data to the trained version of the autoencoder that corresponds to an amino acid sequence of a base protein. The encoding component of the trained autoencoder can generate code data based on the base sequence data that corresponds to a representation of the base sequence data. For example, the code data can include a compressed version of the base sequence data. In one or more examples, the code data can include one or more numerical values. The process 600 can include, at 612, generating an amino acid sequence of a variant protein based on the amino acid sequence of the base protein. In one or more examples, the decoding component can generate the amino acid sequence of the variant protein based on code data generated by the encoding component based on the amino acid sequence of the base protein. The amino acid sequence of the variant protein can have an amount of similarity with respect to the amino acid sequence of the base protein and an amount of difference with respect to the amino acid sequence of the base protein.

In one or more illustrative examples, the code data generated by the encoding component can be modified and the decoding component can produce the amino acid sequence of the variant protein based on the modified code data. In various examples, the code data can be modified by changing one or more numerical values of the code data from an initial value to a modified value. In one or more implementations, an amount of difference between the amino acid sequence of the base protein and the amino acid sequence of the variant protein can correspond to an extent of changes to the numerical values of the code data. The extent of changes to the numerical values of the code data can correspond to a number of the numerical values of the initial version of the code data that are modified with respect to a modified version of the code data. The extent of changes to the numerical values of the code data can also correspond to the magnitude of changes to the numerical values of the initial version of the code data with respect to the modified version of the code data.

In one or more additional examples, the amino acid sequences of a number of variant proteins can be produced using the same numerical values of the code data. For example, a first amino acid sequence of a first variant protein can be produced by the trained version of the autoencoder based on numerical values of the code data and a second amino acid sequence of a second variant protein can be produced by the trained version of the autoencoder based on the same numerical values of the code data. In these scenarios, the trained version of the autoencoder can be produced by providing a training dataset of amino acid sequences to the encoding component that are unable to be reproduced to a threshold amount of sequence identity by the decoding component based on code data generated by the encoding component according to the amino acid sequences of the training dataset. In one or more illustrative examples, the threshold amount of sequence identity in these instances can be at least 95%, at least 97%, at least 98%, at least 99%, or at least 99.5%.

Figure 7:
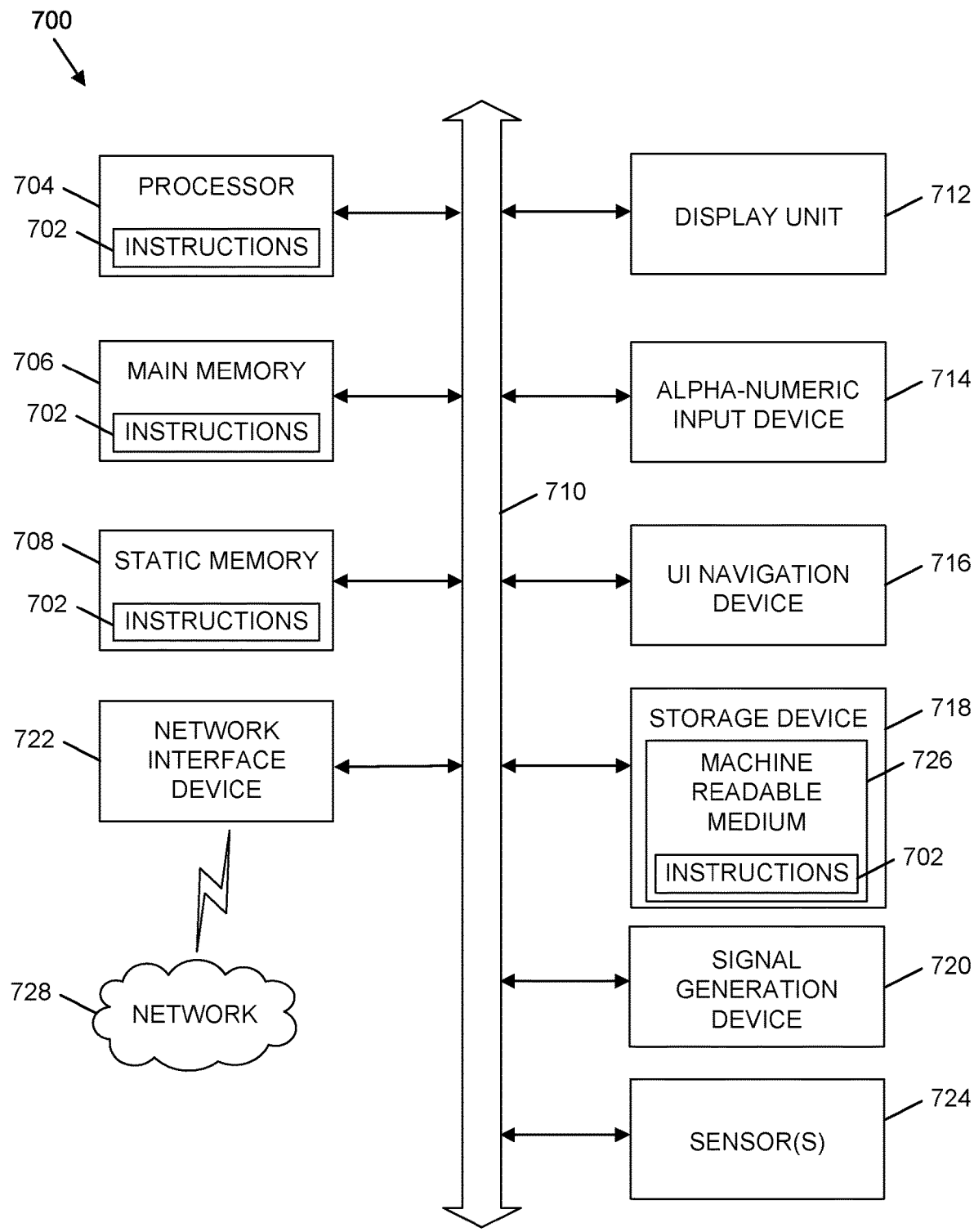
FIG. 7 illustrates a diagrammatic representation of a machine in the form of a computer system within which a set of instructions may be executed for causing the machine to perform any one or more of the methodologies discussed herein, according to an example embodiment.

FIG. 7 illustrates a diagrammatic representation of a machine 700 in the form of a computer system within which a set of instructions may be executed for causing the machine 700 to perform any one or more of the methodologies discussed herein, according to an example, according to an example embodiment. Specifically, FIG. 7 shows a diagrammatic representation of the machine 700 in the example form of a computer system, within which instructions 702 (e.g., software, a program, an application, an applet, an app, or other executable code) for causing the machine 700 to perform any one or more of the methodologies discussed herein may be executed. For example, the instructions 702 may cause the machine 700 to implement the frameworks 100, 200, 300, 400, described with respect to FIGS. 1, 2, 3, and 4, respectively, and to execute the methods 500, 600 described with respect to FIGS. 5 and 6, respectively.

The instructions 702 transform the general, non-programmed machine 700 into a particular machine 700 programmed to carry out the described and illustrated functions in the manner described. In alternative embodiments, the machine 700 operates as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 702, sequentially or otherwise, that specify actions to be taken by the machine 700. Further, while only a single machine 700 is illustrated, the term "machine" shall also be taken to include a collection of machines 700 that individually or jointly execute the instructions 702 to perform any one or more of the methodologies discussed herein.

Examples of machine 700 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 700) and software architectures that can be deployed in example embodiments.

In an example, the machine 700 can operate as a standalone device or the machine 700 can be connected (e.g., networked) to other machines.

In a networked deployment, the machine 700 can operate in the capacity of either a server or a client machine in server-client network environments. In an example, machine 700 can act as a peer machine in peer-to-peer (or other distributed) network environments. The machine 700 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 700. Further, while only a single machine 700 is illustrated, the term "computing device" shall also be taken to include any collection of machines that individually or jointly execute a set (or multiple sets) of instructions to perform any one or more of the methodologies discussed herein.

Example machine 700 can include a processor 704 (e.g., a central processing unit CPU), a graphics processing unit (GPU) or both), a main memory 706 and a static memory 708, some or all of which can communicate with each other via a bus 710. The machine 700 can further include a display unit 712, an alphanumeric input device 714 (e.g., a keyboard), and a user interface (UI) navigation device 716 (e.g., a mouse). In an example, the display unit 712, input device 714 and UI navigation device 716 can be a touch screen display. The machine 700 can additionally include a storage device (e.g., drive unit) 718, a signal generation device 720 (e.g., a speaker), a network interface device 722, and one or more sensors 724, such as a global positioning system (GPS) sensor, compass, accelerometer, or another sensor.

The storage device 718 can include a machine readable medium 726 on which is stored one or more sets of data structures or instructions 702 (e.g., software) embodying or utilized by any one or more of the methodologies or functions described herein. The instructions 702 can also reside, completely or at least partially, within the main memory 706, within static memory 708, or within the processor 704 during execution thereof by the machine 700. In an example, one or any combination of the processor 704, the main memory 706, the static memory 708, or the storage device 718 can constitute machine readable media.

While the machine readable medium 726 is illustrated as a single medium, the term "machine readable medium" can include a single medium or multiple media (e.g., a centralized or distributed database, and/or associated caches and servers) that configured to store the one or more instructions 702. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine-readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 702 can further be transmitted or received over a communications network 728 using a transmission medium via the network interface device 722 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

As used herein, a "component" in this context, refers to at least one of a device, physical entity, group of computer-readable instructions, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example implementations, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A numbered non-limiting list of aspects of the present subject matter is presented below.

Aspect 1. A method comprising: performing, by a computing system including one or more computing devices having one or more processors and memory, a first training process using a first training dataset to produce a trained generating component of a generative adversarial network, the first training dataset including a first plurality of amino acid sequences of first proteins; producing, by the computing system, a second training dataset including a second plurality of amino acid sequences of second proteins, generating, by the computing system, an autoencoder that includes an encoding component and a decoding component, the decoding component comprising the trained generating component of the generative adversarial network; performing, by the computing system, a second training process using the second training dataset to generate a trained version of the autoencoder, the trained version of the autoencoder including a trained version of the encoding component that generates code data, the code data representing one or more amino acid sequences of the second training dataset; providing, by the computing system, base sequence data to the trained version of the autoencoder, the base sequence data including a first amino acid sequence of a base protein; and generating, by the computing system, variant sequence data that includes a second amino acid sequence of a variant protein based on the code data, the second amino acid sequence having an amount of similarity with the respect to the first amino acid sequence and an amount of difference with respect to the first amino acid sequence.

Aspect 2. The method of aspect 1, further comprising: modifying, by the computing system, the code data to produce modified code data, wherein the modified code data is used by the decoding component to generate the second amino acid sequence.

Aspect 3. The method of aspect 1 or 2, wherein the second amino acid sequence has at least a threshold amount of identity with respect to the first amino acid sequence.

Aspect 4. The method of any one of aspects 1-3, wherein the second training dataset is produced by the trained generating component.

Aspect 5. The method of claim any one of aspects 1-4, further comprising: determining, by the computing system and during the first training process, code data by the encoding component of the autoencoder based on an amino acid sequence of the first training dataset obtained by the encoding component; generating, by the computing system and during the first training process, an additional amino acid sequence by the decoding component; determining, by the computing system and during the first training process, a measure of differences between the amino acid sequence and the additional amino acid sequence; and modifying, by the computing system and during the first training process, one or more computational layers of the encoding component based on the measure of differences between the amino acid sequence and the additional amino acid sequence.

Aspect 6. The method of any one of aspects 1-5, wherein first computational layers of the decoding component are unchanged during the first training process and second computational layers of the encoding component are modified during the first training process.

Aspect 7. The method of any one of aspects 1-6, further comprising: obtaining, by the computing system, a third training dataset that includes a third plurality of amino acid sequences of third proteins, the third proteins including a greater number of proteins having at least one of a structural feature or a biophysical property than the first plurality of first proteins included in the first training dataset; performing, by the computing system, a third training process for a generative adversarial network that includes the trained generating component; and producing, by the computing system, an additional trained generating component in relation to the third training process using the third training dataset, the additional trained generating component generating a plurality of amino acid sequences of a first group of proteins having a greater proportion of proteins including at least one of the structural feature or the biophysical property than a second group of proteins corresponding to additional amino acid sequences generated by the trained generating component.

Aspect 8. The method of aspect 7, further comprising: generating, by the computing system, and additional autoencoder that includes the trained version of the encoding component and an additional decoding component that includes the additional trained generating component; and performing, by the computing system, a fourth training process to generate an additional trained version of the autoencoder including an additional trained version of the encoding component using a fourth training dataset that includes a fourth plurality of amino acid sequences of fourth proteins.

Aspect 9. The method of aspect 8, further comprising: providing, by the computing system, additional base sequence data to the additional trained version of the encoding component, the additional base sequence data corresponding to an additional amino acid sequence of an additional base protein; generating, by the computing system and using the additional trained version of the encoding component, additional code data based on the additional base sequence data; and generating, by the computing system and using the additional decoding component, additional variant sequence data that includes a plurality of additional amino acid sequences that correspond to a plurality of additional variant proteins of the additional base protein, the plurality of additional variant proteins having at least a threshold probability of including at least one of the structural feature or the biophysical property.

Aspect 10. The method of any one of aspects 1-9, wherein the base protein includes at least a portion of an antibody.

Aspect 11. The method of any one of aspects 1-10, wherein: the variant sequence data includes a plurality of additional amino acid sequences of a plurality of additional proteins, individual additional amino acid sequences of the plurality of additional amino acid sequences having at least an additional amount of similarity with respect to the first amino acid sequence and an additional amount of difference with respect to the first amino acid sequence; and the method further comprising: generating, by the computing system, a first additional amino acid sequence of the plurality of additional amino acid sequences using numerical values of the code data; and generating, by the computing system, a second additional amino acid sequence of the plurality of additional amino acid sequences using the numerical values of the code data, the second additional amino acid sequence being different from the first additional amino acid sequence.

Aspect 12. A computing system comprising: one or more hardware processors; and one or more non-transitory computer readable media storing computer-executable instructions that, when executed by the one or more hardware processors, cause the one or more processor to perform operations comprising: performing a first training process using a first training dataset to produce a trained generating component of a generative adversarial network, the first training dataset including a first plurality of amino acid sequences of first proteins; producing a second training dataset including a second plurality of amino acid sequences of second proteins, generating an autoencoder that includes an encoding component and a decoding component, the decoding component comprising the trained generating component of the generative adversarial network; performing a second training process using the second training data set to generate a trained version of the autoencoder, the trained version of the autoencoder including a trained version of the encoding component that generates code data, the code data representing one or more amino acid sequences of the second training dataset; providing base sequence data to the trained version of the autoencoder, the base sequence data including a first amino acid sequence of a base protein; and generating, by the computing system, variant sequence data that includes a second amino acid sequence of a variant protein based on the code data, the second amino acid sequence having an amount of similarity with the respect to the first amino acid sequence and an amount of difference with respect to the first amino acid sequence.

Aspect 13. The computing system of aspect 12, wherein the one or more non-transitory computer readable media store additional computer-executable instructions that, when executed by the one or more hardware processors, cause the one or more processor to perform additional operations comprising: modifying the code data to produce modified code data, wherein the modified code data is used by the decoding component to generate the second amino acid sequence.

Aspect 14. The computing system of aspect 12 or 13, wherein the second amino acid sequence has at least a threshold amount of identity with respect to the first amino acid sequence.

Aspect 15. The computing system of any one of aspects 12-14, wherein the second training dataset is produced by the trained generating component.

Aspect 16. The computing system of any one of aspects 12-15, wherein the one or more non-transitory computer readable media store additional computer-executable instructions that, when executed by the one or more hardware processors, cause the one or more processor to perform additional operations comprising: determining, during the first training process, code data by the encoding component of the autoencoder based on an amino acid sequence of the first training dataset obtained by the encoding component; generating, during the first training process, an additional amino acid sequence by the decoding component; determining, by the computing system and during the first training process, a measure of differences between the amino acid sequence and the additional amino acid sequence; and modifying, during the first training process, one or more computational layers of the encoding component based on the measure of differences between the amino acid sequence and the additional amino acid sequence.

Aspect 17. The computing system of any one of aspects 12-16, wherein first computational layers of the decoding component are unchanged during the first training process and second computational layers of the encoding component are modified during the first training process.

Aspect 18. The computing system of any one of aspects 12-17, wherein the one or more non-transitory computer readable media store additional computer-executable instructions that, when executed by the one or more hardware processors, cause the one or more processor to perform additional operations comprising: obtaining a third training dataset that includes a third plurality of amino acid sequences of third proteins, the third proteins including a greater number of proteins having at least one of a structural feature or a biophysical property than the first plurality of first proteins included in the first training dataset; performing a third training process for a generative adversarial network that includes the trained generating component; and producing an additional trained generating component in relation to the third training process using the third training dataset, the additional trained generating component generating a plurality of amino acid sequences of a first group of proteins having a greater proportion of proteins including at least one of the structural feature or the biophysical property than a second group of proteins corresponding to additional amino acid sequences generated by the trained generating component.

Aspect 19. The computing system of aspect 18, wherein the one or more non-transitory computer readable media store additional computer-executable instructions that, when executed by the one or more hardware processors, cause the one or more processor to perform additional operations comprising: generating an additional autoencoder that includes the trained version of the encoding component and an additional decoding component that includes the additional trained generating component; and performing a fourth training process to generate an additional trained version of the autoencoder including an additional trained version of the encoding component using a fourth training dataset that includes a fourth plurality of amino acid sequences of fourth proteins.

Aspect 20. The method of aspect 19, wherein the one or more non-transitory computer readable media store additional computer-executable instructions that, when executed by the one or more hardware processors, cause the one or more processor to perform additional operations comprising: providing additional base sequence data to the additional trained version of the encoding component, the additional base sequence data corresponding to an additional amino acid sequence of an additional base protein; generating, using the additional trained version of the encoding component, additional code data based on the additional base sequence data; and generating, using the additional decoding component, additional variant sequence data that includes a plurality of additional amino acid sequences that correspond to a plurality of additional variant proteins of the additional base protein, the plurality of additional variant proteins having at least a threshold probability of including at least one of the structural feature or the biophysical property.

Aspect 21. The computing system of any one of aspects 12-20, wherein the base protein includes at least a portion of an antibody.

Aspect 22. The computing system of any one of aspects 12-21, wherein: the variant sequence data includes a plurality of additional amino acid sequences of a plurality of additional proteins, individual additional amino acid sequences of the plurality of additional amino acid sequences having at least an additional amount of similarity with respect to the first amino acid sequence and an additional amount of difference with respect to the first amino acid sequence; and the one or more non-transitory computer readable media store additional computer-executable instructions that, when executed by the one or more hardware processors, cause the one or more processor to perform additional operations comprising: generating a first additional amino acid sequence of the plurality of additional amino acid sequences using numerical values of the code data; and generating, by the computing system, a second additional amino acid sequence of the plurality of additional amino acid sequences using the numerical values of the code data, the second additional amino acid sequence being different from the first additional amino acid sequence.

Aspect 23. A computing system comprising: one or more hardware processors; and one or more non-transitory computer readable media storing computer-executable instructions that, when executed by the one or more hardware processors, cause the one or more processor to perform operations comprising: generating code data by an encoding component of an autoencoder, the code data corresponding to a representation of a first amino acid sequence of a base protein that is provided as input to the encoding component; modifying the code data to produce modified code data; providing the modified code data to a decoding component of the autoencoder, the decoding component including a generating component of a generative adversarial network; and generating, by the decoding component, a second amino acid sequence of a variant protein based on the modified code data, the second amino acid sequence having one or more positions with different amino acids than one or more corresponding positions of the first amino acid sequence of the base protein.

Aspect 24. The computing system of aspect 23, wherein the code data includes a plurality of numerical values.

Aspect 25. The computing system of aspect 24, wherein the one or more non-transitory computer readable media storing additional computer-executable instructions that, when executed by the one or more hardware processors, cause the one or more processor to perform additional operations comprising: modifying one or more numerical values of the plurality of numerical values to produce the modified code data.

Aspect 26. The computing system of aspect 24, wherein an extent of differences between the second amino acid sequence of the variant protein and the first amino acid sequence of the base protein is based on at least one of a number of the plurality of numerical values modified to produce the modified code data or a magnitude of change to individual numerical values of the one or more numerical values.

Aspect 27. A method comprising: generating by a computing system including one or more computing devices having one or more processors and memory, code data by an encoding component of an autoencoder, the code data corresponding to a representation of a first amino acid sequence of a base protein that is provided as input to the encoding component; modifying, by the computing system, the code data to produce modified code data; providing, by the computing system, the modified code data to a decoding component of the autoencoder, the decoding component including a generating component of a generative adversarial network; and generating, by the computing system and using the decoding component, a second amino acid sequence of a variant protein based on the modified code data, the second amino acid sequence having one or more positions with different amino acids than one or more corresponding positions of the first amino acid sequence of the base protein.

Aspect 28. The method of aspect 27, wherein the code data includes a plurality of numerical values.

Aspect 29. The method of aspect 27 or 28, comprising modifying, by the computing system, one or more numerical values of the plurality of numerical values to produce the modified code data.

Aspect 30. The method of any one of aspects 27-29, wherein an extent of differences between the second amino acid sequence of the variant protein and the first amino acid sequence of the base protein is based on at least one of a number of the plurality of numerical values modified to produce the modified code data or a magnitude of change to individual numerical values of the one or more numerical values.

What is claimed is:

1. A method comprising:
performing, by a computing system including one or more computing devices having one or more processors and memory, a first training process using a first training dataset to produce a trained generating component of a generative adversarial network, the first training dataset including a first plurality of amino acid sequences of first proteins;
producing, by the computing system, a second training dataset including a second plurality of amino acid sequences of second proteins,
generating, by the computing system, an autoencoder that includes an encoding component and a decoding component, the decoding component comprising the trained generating component of the generative adversarial network;
performing, by the computing system, a second training process using the second training dataset to generate a trained version of the autoencoder, the trained version of the autoencoder including a trained version of the encoding component that generates code data, the code data representing one or more amino acid sequences of the second training dataset;
providing, by the computing system, base sequence data to the trained version of the autoencoder, the base sequence data including a first amino acid sequence of a base protein; and
generating, by the computing system, variant sequence data that includes a second amino acid sequence of a variant protein based on the code data, the second amino acid sequence having an amount of similarity with respect to the first amino acid sequence and an amount of difference with respect to the first amino acid sequence.

2. The method of claim 1, further comprising:
modifying, by the computing system, the code data to produce modified code data, wherein the modified code data is used by the decoding component to generate the second amino acid sequence.

3. The method of claim 1, wherein the second amino acid sequence has at least a threshold amount of identity with respect to the first amino acid sequence.

4. The method of claim 1, wherein the second training dataset is produced by the trained generating component.

5. The method of claim 1, further comprising:
determining, by the computing system and during the first training process, code data by the encoding component of the autoencoder based on an amino acid sequence of the first training dataset obtained by the encoding component;
generating, by the computing system and during the first training process, an additional amino acid sequence by the decoding component;
determining, by the computing system and during the first training process, a measure of differences between the amino acid sequence and the additional amino acid sequence; and
modifying, by the computing system and during the first training process, one or more computational layers of the encoding component based on the measure of differences between the amino acid sequence and the additional amino acid sequence.

6. The method of claim 1, wherein first computational layers of the decoding component are unchanged during the first training process and second computational layers of the encoding component are modified during the first training process.

7. The method of claim 1, further comprising:
obtaining, by the computing system, a third training dataset that includes a third plurality of amino acid sequences of third proteins, the third proteins including a greater number of proteins having at least one of a structural feature or a biophysical property than the first proteins included in the first training dataset;
performing, by the computing system, a third training process for a generative adversarial network that includes the trained generating component; and
producing, by the computing system, an additional trained generating component in relation to the third training process using the third training dataset, the additional trained generating component generating a plurality of amino acid sequences of a first group of proteins having a greater proportion of proteins including at least one of the structural feature or the biophysical property than a second group of proteins corresponding to additional amino acid sequences generated by the trained generating component.

8. The method of claim 7, further comprising:
generating, by the computing system, an additional autoencoder that includes the trained version of the encoding component and an additional decoding component that includes the additional trained generating component; and
performing, by the computing system, a fourth training process to generate an additional trained version of the autoencoder including an additional trained version of the encoding component using a fourth training dataset that includes a fourth plurality of amino acid sequences of fourth proteins.

9. The method of claim 8, further comprising:
providing, by the computing system, additional base sequence data to the additional trained version of the encoding component, the additional base sequence data corresponding to an additional amino acid sequence of an additional base protein;
generating, by the computing system and using the additional trained version of the encoding component, additional code data based on the additional base sequence data; and
generating, by the computing system and using the additional decoding component, additional variant sequence data that includes a plurality of additional amino acid sequences that correspond to a plurality of additional variant proteins of the additional base protein, the plurality of additional variant proteins having at least a threshold probability of including at least one of the structural feature or the biophysical property.

10. The method of claim 1, wherein the base protein includes at least a portion of an antibody.

11. The method of claim 1, wherein:
the variant sequence data includes a plurality of additional amino acid sequences of a plurality of additional proteins, individual additional amino acid sequences of the plurality of additional amino acid sequences having at least an additional amount of similarity with respect to the first amino acid sequence and an additional amount of difference with respect to the first amino acid sequence; and the method further comprising:
generating, by the computing system, a first additional amino acid sequence of the plurality of additional amino acid sequences using numerical values of the code data; and
generating, by the computing system, a second additional amino acid sequence of the plurality of additional amino acid sequences using the numerical values of the code data, the second additional amino acid sequence being different from the first additional amino acid sequence.

12. A computing system comprising:
one or more hardware processors; and
one or more non-transitory computer readable media storing computer-executable instructions that, when executed by the one or more hardware processors, cause the one or more hardware processors to perform operations comprising:
generating code data by an encoding component of an autoencoder, the code data corresponding to a representation of a first amino acid sequence of a base protein that is provided as input to the encoding component;
modifying the code data to produce modified code data;
providing the modified code data to a decoding component of the autoencoder, the decoding component including a generating component of a generative adversarial network; and
generating, by the decoding component, a second amino acid sequence of a variant protein based on the modified code data, the second amino acid sequence having one or more positions with different amino acids than one or more corresponding positions of the first amino acid sequence of the base protein.

13. The system of claim 12, wherein the code data includes a plurality of numerical values.

14. The system of claim 13, wherein the one or more non-transitory computer readable media storing additional computer-executable instructions that, when executed by the one or more hardware processors, cause the one or more hardware processors to perform additional operations comprising:
modifying one or more numerical values of the plurality of numerical values to produce the modified code data.

15. The system of claim 13, wherein an extent of differences between the second amino acid sequence of the variant protein and the first amino acid sequence of the base protein is based on at least one of a number of the plurality of numerical values modified to produce the modified code data or a magnitude of change to individual numerical values of the plurality of numerical values.

* * * * *